(12) United States Patent
Bevilacqua et al.

(10) Patent No.: US 9,017,730 B2
(45) Date of Patent: Apr. 28, 2015

(54) COMPOSITIONS AND USES OF MATERIALS WITH HIGH ANTIMICROBIAL ACTIVITY AND LOW TOXICITY

(71) Applicants: The Regents of the University of California, Oakland, CA (US); Amicrobe, Inc., Pasadena, CA (US)

(72) Inventors: Michael P. Bevilacqua, Boulder, CO (US); Diego Benitez, Los Angeles, CA (US); Timothy J. Deming, Los Angeles, CA (US); Jarrod A. Hanson, Los Angeles, CA (US); Lucas Koziol, Penngrove, CA (US)

(73) Assignees: The Regents of the University of California, Oakland, CA (US); Amicrobe, Inc., Pasadena, CA (US)

( * ) Notice: Subject to any disclaimer, the term of this patent is extended or adjusted under 35 U.S.C. 154(b) by 0 days.

(21) Appl. No.: 13/776,221

(22) Filed: Feb. 25, 2013

(65) Prior Publication Data

US 2013/0267458 A1    Oct. 10, 2013

Related U.S. Application Data

(63) Continuation of application No. PCT/US2011/048869, filed on Aug. 23, 2011.

(60) Provisional application No. 61/376,195, filed on Aug. 23, 2010.

(51) Int. Cl.

| | |
|---|---|
| *A61K 9/14* | (2006.01) |
| *A61P 43/00* | (2006.01) |
| *C07K 14/00* | (2006.01) |
| *A23L 3/3526* | (2006.01) |
| *A61K 38/02* | (2006.01) |
| *A61K 9/00* | (2006.01) |
| *A61K 47/02* | (2006.01) |
| *A61K 9/107* | (2006.01) |
| *A01N 37/18* | (2006.01) |
| *A61K 38/16* | (2006.01) |
| *A61K 45/06* | (2006.01) |

(52) U.S. Cl.
CPC ............ *C07K 14/001* (2013.01); *A23L 3/3526* (2013.01); *A61K 38/02* (2013.01); *A61K 9/0019* (2013.01); *A61K 47/02* (2013.01); *A61K 9/107* (2013.01); *A01N 37/18* (2013.01); *A61K 38/16* (2013.01); *A61K 45/06* (2013.01)

(58) Field of Classification Search
None
See application file for complete search history.

(56) References Cited

U.S. PATENT DOCUMENTS 7,279,458 B2 * 10/2007 Fatheree et al. ............... 514/2.9
2007/0190110 A1 * 8/2007 Pameijer et al. ............. 424/423
2008/0166388 A1   7/2008 Palecek et al.
2009/0208548 A1   8/2009 Mason et al.
2010/0003336 A1 * 1/2010 Deming et al. ............. 424/491

OTHER PUBLICATIONS

Picout et al (2003) The Scientific World Journal 3:105-121.*
Picout et al., "Rheology of Biopolymer Solutions and Gels," The Scientific World Journal (2003) 3, 105-121.
Timothy J. Deming, "Synthetic polypeptides for biomedical applications", Prog. Polym. Sci., 2007. vol. 32, pp. 858-875.
International Search Report issued in PCT Application No. PCT/US2011/048869 dated Sep. 28, 2012.
Bani-Jaber et al., Efficacy of the Antimicrobial Peptide Nisin in Emulsifying Oil in Water. Journal of Food Science, 2000. 65(3): p. 502-506.
Boyce et al., Guideline for Hand Hygiene in Health-Care Settings. Morbidity and Mortality Weekly Report, 2002. 51(RR-16): p. 1-54.
Brogden et al., Antimicrobial peptides: pore formers or metabolic inhibitors in bacteria? Nat Rev Microbiol, 2005. 3(3): p. 238-250.
Deming et al., Methodologies for preparation of synthetic block copolypeptides: materials with future promise in drug delivery. Advanced Drug Delivery Reviews, 2002. 54: p. 1145-1155.
Deming et al., Polypeptide and Polypeptide Hybrid Copolymer Synthesis via NCA Polymerization. ChemInform, 2007. 38(5): p. no-no.
Eberlein et al., Clinical use of polihexanide on acute and chronic wounds for antisepsis and decontamination. Skin Pharmacology and Physiology, 2010. 23 Suppl: p. 45-51.
Epand et al., Dual mechanism of bacterial lethality for a cationic sequence-random copolymer that mimics host-defense antimicrobial peptides. J Mol Biol, 2008. 379(1): p. 38-50.
Gabriel et al., Infectious Disease: Connecting Innate Immunity to Biocidal Polymers. Mater Sci Eng R Rep, 2007. 57(1-6): p. 28-64.
Gilbert et al., Cationic antiseptics: diversity of action under a common epithet. Journal of Applied Microbiology, 2005. 99(4): p. 703-715.
Goodson et al., Characterization of novel antimicrobial peptoids. Antimicrob Agents Chemother, 1999. 43(6): p. 1429-34.
Hancock et al., Cationic peptides: a new source of antibiotics. Trends Biotechnol, 1998. 16(2): p. 82-8.
Hanson et al., Nanoscale double emulsions stabilized by single-component block copolypeptides. Nature, 2008. 455: p. 85-89.
Higgins et al., Resistance to antibiotics and biocides among non-fermenting Gram-negative bacteria. Clinical Microbiological Infections, 2001. 7: p. 308-315.
Ho et al., Improving emulsifying activity of [var epsilon]-polylysine by conjugation with dextran through the Maillard reaction. Food Chemistry, 2000. 68(4): p. 449-455.
Ilker et al., Tuning the hemolytic and antibacterial activities of amphiphilic polynorbornene derivatives. J Am Chem Soc, 2004. 126(48): p. 15870-5.
Kuroda et al., The role of hydrophobicity in the antimicrobial and hemolytic activities of polymethacrylate derivatives. Chemistry, 2009. 15(5): p. 1123-33.
Lam et al., D-amino acids govern stationary phase cell wall remodeling in bacteria. Science, 2009. 325(5947): p. 1552-5.

(Continued)

*Primary Examiner* — Jean Witz
*Assistant Examiner* — Mindy Newman
(74) *Attorney, Agent, or Firm* — Venable LLP; Stefan J. Kirchanski

(57) ABSTRACT

Improved synthetic copolypeptide antimicrobials contain cationic amino acid residues and may be based on a blocky sequence. These antimicrobials show low mammalian toxicity and may undergo directed self-assembly. The inventive synthetic copolypeptides are useful in treatment of wounds and other infections.

20 Claims, 40 Drawing Sheets

(56) References Cited

OTHER PUBLICATIONS

Landman, et al., Polymyxins revisited. Clin Microbiol Rev, 2008. 21(3): p. 449-65.

Lio et al., Topical antibacterial agents. Infectious Disease Clinics of North America, 2009. 23(4): p. 945-963.

Liu et al., De novo design, synthesis, and characterization of antimicrobial beta-peptides. J Am Chem Soc, 2001. 123(31): p. 7553-9.

Liu et al., Nontoxic membrane-active antimicrobial arylamide oligomers. Angew Chem Int Ed Engl, 2004. 43(9): p. 1158-62.

Oie et al., Microbial contamination of antiseptics and disinfectants. Am J Infect Control, 1996. 24(5): p. 389-95.

Porter et al., Mimicry of host-defense peptides by unnatural oligomers: antimicrobial beta-peptides. J Am Chem Soc, 2002. 124(25): p. 7324-30.

Salick et al., Inherent antibacterial activity of a peptide-based beta-hairpin hydrogel. J Am Chem Soc, 2007. 129(47): p. 14793-9.

Stickler et al., Antiseptic and antibiotic resistance in Gram-negative bacteria causing urinary tract infection. J Clin Pathol, 1980. 33(3): p. 288-96.

Tew et al., Antimicrobial activity of an abiotic host defense peptide mimic. Biochim Biophys Acta, 2006. 1758(9): p. 1387-92.

Wang et al., Antimicrobial and Hemolytic Activities of Copolymers with Cationic and Hydrophobic Groups: A Comparison of Block and Random Copolymers. Macromolecular Bioscience, 2011: p. n/a-n/a.

Wyrsta et al., A parallel synthetic approach for the analysis of membrane interactive copolypeptides. J Am Chem Soc, 2001. 123(51): p. 12919-20.

Wyrsta et al., Synthesis and studies of polypeptide materials: Self-assembled block copolypeptide amphiphiles, DNA-condensing block copolypeptides and membrane-interactive random copolypeptides, 2002, University of California, Santa Barbara. p. 125.

Yang et al., Biocompatibility of amphiphilic diblock copolypeptide hydrogels in the central nervous system. Biomaterials, 2009. 30: p. 2881-2898.

Yeaman et al., Mechanisms of antimicrobial peptide action and resistance. Pharmacol Rev, 2003. 55(1): p. 27-55.

Zaiou et al., Multifunctional antimicrobial peptides: therapeutic targets in several human diseases. J Mol Med (Berl), 2007. 85(4): p. 317-29.

Zasloff et al., Antimicrobial peptides of multicellular organisms. Nature, 2002. 415(6870): p. 389-95.

Zhou et al., High potency and broad-spectrum antimicrobial peptides synthesized via ring-opening polymerization of alpha-aminoacid-N-carboxyanhydrides. Biomacromolecules, 2010. 11(1): p. 60-7.

\* cited by examiner

| POLYPEPTIDE | PDI[a] | $M_n$-(X $10^3$)[b] |
|---|---|---|
| $K_{55}L_X$ SERIES | | |
| $K_{55}L_5$ | 1.09 | 9.8 |
| $K_{55}L_{10}$ | 1.09 | 10.4 |
| $K_{55}L_{15}$ | 1.09 | 10.9 |
| $K_{55}L_{20}$ | 1.09 | 11.5 |
| $K_{55}L_{25}$ | 1.09 | 12.1 |
| $K_{55}L_{30}$ | 1.09 | 12.6 |
| $K_{55}(rac\text{-}L)_X$ SERIES | | |
| $K_{55}(rac\text{-}L)_5$ | 1.12 | 9.6 |
| $K_{55}(rac\text{-}L)_{10}$ | 1.12 | 10.2 |
| $K_{55}(rac\text{-}L)_{20}$ | 1.12 | 11.3 |
| $K_{55}(rac\text{-}L)_{30}$ | 1.12 | 12.4 |
| RANDOM $K_{55}(rac\text{-}L)_X$ AND $K_{55}L_X$ SERIES | | |
| RANDOM $K_{55}L_{20}$ | 1.13 | 10.3 |
| RANDOM $K_{55}(rac\text{-}L)_5$ | 1.14 | 10 |
| RANDOM $K_{55}(rac\text{-}L)_{10}$ | 1.18 | 10.2 |
| RANDOM $K_{55}(rac\text{-}L)_{20}$ | 1.16 | 12.2 |
| RANDOM $K_{55}(rac\text{-}X)_Y$ | | |
| $K_{55}(rac\text{-}I)_{20}$ | 1.12 | 11.3 |
| $K_{55}(rac\text{-}L/F)_{20}$ | 1.12 | 11.7 |
| $K_{55}(rac\text{-}V)_{20}$ | 1.12 | 11 |
| $K_{55}(rac\text{-}A)_{20}$ | 1.12 | 10.5 |

FROM FIG. 33A

| LONG $K_X(rac\text{-}L)_Y$ AND RANDOM $K_X(rac\text{-}L)_Y$ SERIES | | |
|---|---|---|
| $K_{90}(rac\text{-}L)_{30}$ | 1.27 | 18.1 |
| RANDOM $K_{90}(rac\text{-}L)_{30}$ | 1.17 | 18.3 |
| $K_{120}(rac\text{-}L)_{40}$ | 1.16 | 24.3 |
| RANDOM $K_{120}(rac\text{-}L)_{40}$ | 1.07 | 23.5 |
| $K_{150}(rac\text{-}L)_{50}$ | 1.23 | 30.3 |
| RANDOM $K_{150}(rac\text{-}L)_{50}$ | 1.23 | 31.3 |
| POLYPEPTIDE | $PDI^a$ | $M_n (\times 10^3)^b$ |
| $K_X$ | | |
| $K_{80}$ | 1.2 | 13.2 |
| $K_{256}$ | 1.2 | 42.4 |
| LONG $K_X L_Y$ SERIES | | |
| $K_{180}L_{20}$ | 1.30 | 40.2 |
| $K_{190}L_{10}$ | 1.23 | 41.2 |
| $R^H_{55}$ | | |
| $R^H_{55}(rac\text{-}L)_{20}{}^c$ | - | 13.6 |
| PEG | | |
| $PEG_{205}(rac\text{-}L)_{20}$ | 1.06 | 11.3 |
| E SERIES | | |
| $E_{64}(rac\text{-}L)_{20}$ | 1.17 | 11.9 |
| $E_{180}L_{20}$ | 1.34 | 30.3 |

FIG. 33B

| PEPTIDE | E. COLI 11229 | E. COLI O157:H7 |
|---|---|---|
| BLOCK $K_{55}L_{20}$ | 1 | 0.25 |
| BLOCK $K_{55}(rac\text{-}L)_{20}$ | 1 | 1 |
| BLOCK $K_{55}(rac\text{-}L)_{10}$ | 5 | 1 |
| BLOCK $K_{55}(rac\text{-}L/F)_{20}$ | 5 | 1 |
| BLOCK $R^H_{55}(rac\text{-}L)_{20}$ | 30 | 1 |

FIG. 34

| MICROBE | MIC (μg/mL) | | | |
|---|---|---|---|---|
| | $K_{60}L_{20}$ RANDOM | $K_{55}(rac\text{-}L)_{20}$ | $K_{55}(rac\text{-}L)_{10}$ | $K_{55}(rac\text{-}L/F)_{20}$ |
| S. AUREUS | 7.8 | 7.8 | 7.8 | 7.8 |
| L. MONOCYTOGENES | 3.9 | 7.8 | 3.9 | 5.9 |
| S. ENTERICA | 31.3 | 125 | 62.5 | 250 |
| B. CEREUS | 7.8 | 7.8 | 7.8 | 7.8 |
| B. SUBTILIS | 7.8 | 11.7 | 5.9 | 7.8 |
| B. CEREUS ENDOSPORES | 15.6 | 15.6 | 15.6 | 15.6 |
| B. SUBTILIS ENDOSPORES | 250 | 125 | 250 | 250 |

FIG. 35

| | LOG REDUCTION |
|---|---|
| BLOCK $K_{55}(rac\text{-}L)_{20}$ | 0.3 |
| BLOCK $K_{55}(rac\text{-}L)_{20}$ EMULSION | 0.3 |
| BLOCK $(R^H/K)_{55}(rac\text{-}L)_{20}$ | 1.5, 3.0 |
| BLOCK $E_{64}(rac\text{-}L)_{20}$ | 0 |

FIG. 36

| MICROBE | MIC (µg/mL) | | | |
| --- | --- | --- | --- | --- |
| | $K_{60}L_{20}$ RANDOM | $K_{55}(rac\text{-}L)_{20}$ | $K_{55}(rac\text{-}L)_{10}$ | $K_{55}(rac\text{-}L/F)_{20}$ |
| B. SUBTILIS ENDOSPORES | 7.8 | 31.3 | 15.6 | 15.6 |

FIG. 37

|  |  | % CYTOTOXICITY |
|---|---|---|
| $K_{55}(rac\text{-}L)_{20}$ BLOCK | SOLUTION | 92.0 |
|  | EMULSION | 0 |
| $R^H{}_{55}(rac\text{-}L)_{20}$ BLOCK | SOLUTION | 88.4 |
|  | EMULSION | 18.5 |

FIG. 38

| TEG PARAMETER | SALINE | PEPTIDE (10μg/mL) | | | |
|---|---|---|---|---|---|
| | | $K_{180}L_{20}$ | $RK_{55}(rac\text{-}L)_{20}$ | $RH_{55}(rac\text{-}L)_{20}$ | $E_{64}(rac\text{-}L)_{20}$ |
| R TIME (min) | 18.3 ± 3.2 | 11.6 ± 2.0* | 10.8 ± 1.3* | 5.7 ± 0.7* | 18.7 ± 2.5 |
| K TIME (min) | 7.5 ± 1.7 | 5.2 ± 1.0 | 2.9 ± 0.6* | 1.7 ± 0.3* | 7.3 ± 0.8 |
| α ANGLE (°) | 41.5 ± 2.8 | 45.3 ± 2.7 | 59.7 ± 4.7* | 70.9 ± 3.3* | 40.3 ± 1.6 |
| MA (mm) | 53.5 ± 3.3 | 46.6 ± 3.2 | 51.5 ± 0.8 | 60.7 ± 3.5 | 54.8 ± 3.6 |

FIG. 39

COMPOSITIONS AND USES OF MATERIALS WITH HIGH ANTIMICROBIAL ACTIVITY AND LOW TOXICITY

CROSS-REFERENCE TO PRIOR APPLICATIONS

This application claims the benefit and priority of U.S. Provisional Patent Application Ser. No. 61/376,195, filed 23 Aug. 2010, which is incorporated herein by reference to the extent permitted by applicable law.

U.S. GOVERNMENT SUPPORT

Not Applicable.

BACKGROUND OF THE INVENTION

1. Field of the Invention

The current invention relates to compositions of matter that are able to kill (or inhibit) microbes, and have low mammalian toxicity. The current invention also relates to certain compositions and their uses in a variety of settings including but not limited to preservatives, antiseptics, and the prevention and treatment of wound infections, as well as other infectious diseases.

2. Discussion of Related Art

Cationic Antimicrobials have Demonstrated Utility; Toxicity is a Problem.

For over half a century, cationic (positively charged) antimicrobials have been used in a variety of medical and non-medical settings, ranging from systemic antibiotics to industrial cleansers. Cationic antimicrobials bind preferentially to bacterial membranes, which typically display more negative charge than mammalian membranes. This interaction can disrupt membrane function and potentially lead to bacterial cell death. Cationic antimicrobial compounds include certain antibiotics (e.g., polymyxins), bisbiguanides (e.g., chlorhexidine), polymeric biguanides (e.g., polyhexamethylene biguanide), and quaternary ammonium compounds (QAC) (e.g., benzalkonium chloride), as well as natural antimicrobial peptides (AMPs) (e.g., defensins). While each class of cationic antimicrobial compounds has demonstrated antimicrobial activity in one or more settings, toxicity has been a consistent problem.[1-12]

Polymyxins, produced by *Bacillus polymyxa*, are cyclic peptides with hydrophobic tails.[6, 7] The cyclic peptide portion (approx. 10 amino acid residues; positively charged) interacts strongly with negatively charged lipopolysaccharide (LPS) found on the outer membrane of Gram-negative bacteria. The hydrophobic tail is thought to interact with, and in some cases, disrupt the bacterial membrane. Polymyxins have antimicrobial activity against many Gram-negative bacteria, including *Pseudomonas aeniginosa* (*P. aeruginosa*), *Escherichia coli* (*E. coli*), and *Enterobacter* species, but have limited activity against Proteus, most *Serratia*, or Gram-positive bacteria [7]. Significant neurotoxicity and nephrotoxicity have contributed to their limited use as systemic antibiotics [13]. Today, Polymyxins are sometimes used as a last resort for Gram-negative infections that are highly antibiotic resistant, such as those caused by multi-drug resistant *P. aeniginosa*. They are also used as topical antimicrobial agents for small cuts and scrapes of the skin.

Chlorhexidine is widely used in the pre-operative surgical setting as an antiseptic cleanser for general skin cleaning, preoperative bathing, and surgical site preparation [7]. Chlorhexidine is active against a wide range of Gram-positive and Gram-negative bacteria, although resistance by some Gram-negative bacteria (e.g., *P. aeniginosa, Providentia* species) has been reported [5, 10]. Formulations containing 2-4% chiorhexidine appear to be most effective as antimicrobials, but can cause skin irritation. Overall, chlorhexidine is relatively safe when applied to intact skin because minimal amounts of the compound are absorbed. However, due to irritation and toxicity, chlorhexidine is contraindicated for use near the eyes, ears, brain tissues, and meninges [2]. Low concentrations (e.g., 0.05% to 0.12%) are sometimes used as wound washes and oral rinses. Activity is pH dependent, as low pH environments reduce activity. In addition, chiorhexidine is not compatible with anionic compounds (e.g., hard water, soap, alginate) and shows reduced activity in the presence of organic materials (e.g., blood).

Polyhexamethylene biguanide (PHMB) has been used in diverse consumer applications for over 40 years. PHMB is used in swimming pool sanifizers, preservatives of plasticized PVC, and general-purpose environmental biocides [1]. Early production of PHMB resulted in highly polydisperse oligomers with molecular weights ranging from 500-6,000 g/mol. Limited chemical characterization largely precluded early PHMB use in pharmaceutical products. Recent PHMB formulations have been able to address polydispersity. Similar to chlorhexidine, use of PHMB is contraindicated for eyes, ears, brain tissues, meninges, and joints [4].

Quaternary ammonium compounds (QACs) are amphoteric surfactants, typically containing one nitrogen atom linked directly to four alkyl groups, which may vary in hydrophobic structure [1, 2]. QACs are primarily bacteriostatic, but at higher concentrations can be bacteriocidal against certain organisms. QACs are antimicrobial against Gram-positive bacteria, but are less effective against Gram-negative bacteria (e.g., *P. aeruginosa*). Because of weak activity against Gram-negatives, QACs are generally not used in health-care settings for hand antisepsis. Several outbreaks of infection have been traced to QAC compounds contaminated with Gram-negative bacilli [8]. QACs appear to be more susceptible to resistance mechanisms mediated through multidrug efflux pumps. Activity is also greatly reduced in the presence of organic matter.

Natural antimicrobial peptides (AMPS) are often cationic. Natural antimicrobial peptides (AMPs) (typically, less than 50 amino acids) are widely distributed in most species from insects to mammals, and are thought to play key roles in innate immunity [14]. AMPS have demonstrated potent killing inhibition of bacteria, viruses, fungi and parasites [15]. AMPs are thought to be important in preventing and controlling infections. AMPs are heavily deposited at interfaces such as the skin, respiratory tract, and gastrointestinal lining, and are released by white blood cells at sites of inflammation. White blood cells use AMPs as part of their direct killing mechanisms in phagolysosomes. Certain AMPs contribute to the regulation of inflammation and adaptive immunity [15]. In addition, AMPs have demonstrated inhibitory activity against spermatozoa and cancer cells.

Most AMPs share structural characteristics leading to physical, receptor-independent modes of killing [9]. A widely accepted mechanism of action of AMPs is microbial membrane disruption or perturbation (followed sometimes by pore formation) leading to cell death. Typically, AMPs contain positively charged and hydrophobic domains that are spatially segregated-cationic amphiphiles. Substantial hydrophobic content of AMPS (typically, 30 to 60% mole fraction) is an important feature for antimicrobial activity as it "governs the extent to which a peptide can partition into the lipid bilayer" [16]. AMPs that form alpha-helices "frequently exist as extended or unstructured conformers in solution" and become helical "upon interaction with amphipathic phospholipid membranes" [16]. This suggests that the "local environment at the bacterial outer surface and membranes is important and can induce antimicrobial peptide conformational changes that are necessary for peptide attachment to and insertion into the membrane" [3].

Nisin (a bacterially-derived AMP that has been used as a food preservative) was shown to be a weak emulsifying agent for oil-water mixtures, the process being significantly pH- and temperature-dependent [17].

Several natural AMPs and related technologies have been patented. Lehrer and Seisted disclosed AMP sequences analogous to those of defensins isolated from macrophages (U.S. Pat. No. 4,543,252). The magainin class of AMPs, first isolated from the skin of certain frogs, has been described by Zasloff (U.S. Pat. No. 4,810,777). Modified magainins, particularly sequence deletions or substitutions, have also been described (e.g., U.S. Pat. Nos. 4,962,277; 5,221,732; 5912231; and 5,792,831). Selsted and Cullor disclosed bovine indolicidin AMP as a broad-spectrum antimicrobial compound (U.S. Pat. No. 5,324,716).

Synthetic Peptide-Based Cationic Oligomers May Function as Antimicrobials.

Salick and colleagues have disclosed a sequence-specific beta-hairpin peptide (20-mer) which can form an antimicrobial hydrogel in the presence of sufficient salt concentration (US Published Patent Application No. 2011/0171304). When the peptide is "dissolved in water, it remains unfolded and soluble due to the charge repulsion between positively charged side chains." The addition of salt is thought to "screen the side chain-derived charge and allow the peptide to fold" into a beta-hairpin which may "assemble into a network of beta-sheet rich fibrils." The peptide consists of 60% hydrophobic content and contains two arginine residues that seem to be important for effective antimicrobial activity against methicillin-resistant *Staphylococcus aureus* (MRSA). The peptides themselves do not appear to be inherently antimicrobial, as the inventors have reported that "peptide diffusing from the gel is not the active agent." When *S. aureus* was subjected to 100 μM (approx. 230 μg/ml) aqueous solutions (i.e., not hydrogels) of peptide, "bacterial proliferation was minimally affected." Thus, for antimicrobial activity, bacteria must directly contact the hydrogel surface; "folded but not gelled" peptide does not inhibit bacterial proliferation. Similar findings were reported for other closely-related beta-hairpin peptides [18].

Gellman and coworkers have disclosed antimicrobial compositions containing beta-amino acid oligomers (U.S. Pat. Nos. 6,060,585; 6,683,154; US Published Patent Application Nos. 2007/0087404; 2008/0166388) with well-defined secondary structures. The beta-peptides contain ring structures in the peptide backbone which limit conformational flexibility. DeGrado and coworkers have also described antibacterial beta-peptides, containing oligomers (7-mer or shorter) of a tri-beta-peptide (U.S. Pat. No. 6,677,431).

Other synthetic peptide-based compounds that may mimic overall structure of natural AMPs have been described. DeGrado reported amphiphilic sequence-random beta-peptides based on structural properties of the natural AMPs magainin and cecropin [19]. Gellman and coworkers have described a random-sequence, beta-peptide oligomer with an average length of 21 residues, polydispersity index (Mn/Mw) of 1.4, and 40% hydrophobic residues [20]. In other studies, Gellman identified helical beta-peptides [19]. A 60% "hydrophobic face" along the helical cylinder was found to have optimal antimicrobial activity, while a 40% face displayed low activity.

Synthetic Cationic Polymers Comprised of Non-Natural Building Blocks May Function as Antimicrobials.

Several classes of synthetic antimicrobial polymers with non-natural building blocks or repeat-units have been described; they are the subject of a 2007 review by Tew [22]. These polymers are comprised of structures/monomeric units that are not found in nature. These non-natural polymers often feature easy and cost-efficient syntheses, and stability against enzymatic degradation. However, limitations of these and other non-natural polymers may include limited antimicrobial activity, as well as a lack of biocompatibility and biodegradability. Materials in this class are comprised of unnatural building blocks (e.g. aryl amides, highly conjugated aromatic groups) and are considered outside the scope of this invention [21-25]. (For examples, see U.S. Pat. No. 7,173,102; US Published Patent Application Nos. 2008/0176807; 2010/0105703).

Antimicrobial peptoids (N-substituted glycines) have been described by Winter and coworkers [28]. A series of short (3-monomer) peptoids were tested against a broad spectrum of Gram-positive and Gram-negative bacteria, and hemolytic activity (HC50) was lower than antimicrobial activity (minimum inhibitory concentrations, MICs). A representative tri-peptoid protected *S. aureus*-infected mice in vivo in a simple infection model.

Synthetic Methodologies for Copolypeptides (Deming Method).

Traditional synthetic methodologies have precluded the efficient synthesis of oligopeptide libraries with orthogonal (or semi-orthogonal) modification of multiple properties. Important properties to be modified include amino acid sequence, overall chain length, and ratio of cationic to hydrophobic amino acids. Moreover, the practical, cost-effective synthesis of low polydispersity (PDI between 1.0 and 1.4) copolypeptide mixtures has also not been easily accessible [25].

Control over multiple properties, and the ability to create low polydispersity compounds, would allow optimization of multiple structure-function relationships. A major challenge in synthetic polypeptide AMP research is prohibitive production costs in solid-phase synthesis. In addition, significant chemical limitations of both solid-phase and solution-phase synthetic methods include lack of control over chain growth. This leads to chain branching, polydispersity and low product yields.

In 1997, Deming developed well-defined initiators to polymerize amino acid derivatives into oligopeptide chains [25, 26]. This methodology added amino acid monomers to a growing chain in batches. The initiators were transition-metal complexes that allowed controlled synthesis to yield high molecular weight, narrowly-distributed, multi-block polypeptide formulations. The initiators and synthetic methods are well described in the literature and in several patents (U.S. Pat. Nos. 6,680,365; 6,632,922; 6,686,448; 6,818,732; 7,329,727; US Published Patent Application No. 200810125581).

Typically, the synthetic polypeptides have a simple binary composition (e.g., lysine (K), leucine (L) copolymers). Amphiphilic polypeptides contain ionic amino acid monomers (e.g., lysine, arginine (R), glutamate (E)) co-polymerized with neutral hydrophobic amino acids (e.g., leucine, alanine (A)). By variation of method of monomer addition, copolymerizations may be conducted to obtain sequences of amino acid residues along the copolymer chain that are blocky, random, or a combination of both (i.e. blocks of random sequences).

Random Synthetic Copolypeptides in Solution Demonstrate Antimicrobial Activity.

The Deming laboratory has observed antimicrobial activity for a series of water-soluble copolypeptides containing varying ratios of cationic (lysine, (K)) and hydrophobic (leucine (L), isoleucine (I), valine (V), phenylalanine (F), or alanine (A)) amino acids that were randomly arranged [27]. Copolypeptides demonstrated varying antimicrobial activity against *S. aureus* (Gram-positive), *P. aeruginosa* (Gram-negative), and *E. coli* (Gram-negative) in suspension growth assays. Lysine-alanine copolypeptides demonstrated a broad "toxic effect on all three species of bacteria studied" and were concluded to be the "most effective antimicrobial copolymer combination." Circular dichroism spectra of lysine-alanine and lysine-leucine copolypeptides showed "unambiguous random coil conformations when free in solution." This work did not examine the antimicrobial activity of synthetic block sequence copolypeptides or synthetic copolypeptides deliberately formulated as micelles, or incorporated into emulsions/nanoemulsions (also see [28, 29]).

Using Deming synthesis methods, Chan-Park and colleagues recently studied the antimicrobial activity of soluble, random-sequence copolypeptides containing 2-3 different amino acids [26]. Random 25-mer copolypeptides, comprised of lysine-phenylalanine or lysine-phenylalanine-leucine, demonstrated the broadest activity against five microbes and had the lowest MICs. The effects of total peptide length and hydrophobic content on antimicrobial activity were investigated. Lysine-phenylalanine copolypeptide was reported to have "broader antibacterial activity when it is 25 residues long than at shorter or longer length." Optimum hydrophobic content for lysine-phenylalanine compounds (and other random copolypeptides) was found to be about 60%. However, optimized lysine-phenylalanine and lysine-phenylalanine-leucine compounds showed high hemolytic activity compared to other natural and synthetic peptides. The authors suggested that the compounds' "high hydrophobicity (60%) or more hydrophobic species present may have resulted in high toxicity to mammalian red blood cells." In addition, lysine-alanine and lysine-leucine random copolypeptides showed no significant activity against the fungal organism *Candida albicans*. Circular dichroism analysis indicated that lysine-phenylalanine and lysine-phenylalanine-leucine random copolypeptides show "lack of a distinct secondary structure" and do not form alpha-helices or beta-sheets.

Synthetic Copolypeptides can be Formulated to Achieve Hierarchical Structures.

The presence of both polyelectrolyte and hydrophobic domains leads to microphase segregated materials. Resulting superstructures can include multimers in solution, micelles, emulsions (with oil), sheets, vesicles and fibrils that form hydrogels. Self-assembly into different hierarchical structures can be controlled by: varying composition and chain length; varying concentration; presence of L-, D-, or racemic amino acids; and modification of side-chains and chain-termini (e.g. polyethylene glycol (PEG)). Secondary structure of hydrophobic domains (i.e. random coil vs. alpha-helix) plays an important role in superstructure formation. The nature of the hydrophobic domain or polymer segments determines the type of intermolecular interactions that are established between chains. These attractive interactions are balanced by the interactions with the solvent. There exists an equilibrium between the free energy of self-association with the free energy of hydration for each molecule and for each fragment of the supermolecule.

Synthetic copolypeptides can also be designed to form hydrogels. Certain characteristics, such as long-hydrophilic blocks (cationic or anionic) and ordered hydrophobic blocks (e.g., alpha-helical) were shown to favor hydrogel formation. Studies suggest that several synthetic copolypeptide-based hydrogels, including $K_{180}L_{20}$ (and other $K_xL_y$) block copolypeptides, are biocompatible in vivo. Deming et al. previously reported that block copolypeptide hydrogels can serve as tissue scaffolds in the murine central nervous system (CNS) [27]. Hydrogels were injected into mouse forebrain and created 3D gel deposits in vivo. Toxicity, inflammation and gliosis were minimal and similar to saline controls. After 8 weeks, in many cases, copolypeptide deposits were vascularized with cell density similar to adjacent tissue, suggesting hydrogels are supportive of cellular migration and proliferation.

Deming (PCT publication WO 2009/025802) disclosed nanoemulsions and double nanoemulsions stabilized by synthetic block copolypeptides [27]. Antimicrobial activity of the emulsified copolypeptides was not disclosed therein.

Nanoemulsions prepared without copolypeptides can display some antimicrobial activity. Baker and coworkers have focused on the use of nanoemulsions as antimicrobial agents. They reported antimicrobial emulsions stabilized by phosphate-based or other small molecule surfactants (U.S. Pat. Nos. 6,015,832; 6,506,803; 6,559,189; 6,635,676; 5,618,840; 5,547,677; and 5,549,901).

Potential relationships between antimicrobial activity and/or mammalian cell toxicity of cationic amphiphiles and their assembly into higher-order structures are not well understood. Limited relevant information has been reported. For example, the antimicrobial activity of epsilon-poly-lysine (EPL) was slightly reduced by coordination to a lipid and emulsification, relative to free EPL in solution [33].

SUMMARY OF THE INVENTION

The present invention describes compositions of matter and uses of synthetic copolypeptides with high antimicrobial activity (in vitro or in vivo) and low mammalian toxicity. Notably, cationic (positively charged) antimicrobials have been used for more than fifty years in a variety of medical and non-medical settings, ranging from systemic antibiotics to industrial cleansers. Despite substantial efficacy, their use in many medical settings has been limited due to substantial toxicities. This invention overcomes the limitation of the inherent toxicity of cationic antimicrobials. Simply stated, by controlling the relationship between cationic elements and hydrophobic elements, we design materials with high antimicrobial activity and low mammalian toxicity, often taking advantage of unique hierarchical structures. This invention includes the grouping of hydrophilic and/or hydrophobic amino acid residues along a copolypeptide chain into blocky sequences to achieve block amphiphilicity. This differs from facial amphiphilicity that characterizes many natural AMPs, as well as random-sequence and alternating-sequence and specific-sequence synthetic copolypeptides and peptides. For the purposes of this invention, blocky or block-sequence copolypeptides are characterized as copolypeptides consisting of one or more different domains that each contain a contiguous repeat of at least 5 residues of a single amino acid (e.g. lysine or leucine) or amino acid type (cationic or hydrophobic). By contrast, random copolypeptides are characterized as copolypeptides consisting of non-ordered, statistical distributions of two or more different amino acid residues (or amino acid types) within a sequence.

The synthetic copolypeptides of the present invention possess one or more of the following molecular characteristics that distinguish them from previously described natural and synthetic antimicrobials. First, relatively high overall chain length (40 to 250 or more amino acid residues per chain); second, multimeric display of the hydrophilic (typically, cationic) domains; third, relatively low hydrophobic residue content (typically, 40% mole fraction or less); and fourth, self-association/self-assembly through interactions of the hydrophobic domains (often based on block sequence). By way of explanation, without limiting the scope of this invention, it is thought that high antimicrobial activity results from the display of long hydrophilic (cationic) segments, multimeric hydrophilic (cationic) segments, or both, which interact very effectively with anionic (negative) charges at the surface of microbes. Further, by way of explanation without limiting the scope of this invention, it is thought that the relatively low hydrophobe content, the self-associating nature of the hydrophobic domains (often based on block sequence), or both serves to limit tissue exposure to high hydrophobic or high amphipathic material concentrations, thereby decreasing mammalian toxicity. In certain cases, this limited hydrophobe or amphipathic exposure may allow administration of larger quantities of antimicrobial material in vivo, with potential for depot, slow-release effects and greater antimicrobial activity (with less mammalian toxicity) over time.

Without limiting the scope of the present invention, it is recognized that achieving high antimicrobial activity (in vitro or in vivo) and low toxicity may depend on one or more factors, including the following: monomer selection (e.g., specific cations and hydrophobes); spatial distribution of monomers (e.g., blocky vs. random sequences); mole fraction of hydrophobic monomers; optical purity of monomers; ordered vs. disordered hydrophobic domains (e.g., alpha-helical vs. random coil), chemical modification of monomers/residues; hybrid compositions (e.g., copolypeptide-polymer conjugates).

These synthetic copolypeptides can be designed to self-associate/self-assemble, in part, through interactions of poorly solvated hydrophobic regions, that are stabilized by fully dissolved hydrophilic (typically, cationic) domains. Specific examples include preparations involving multimers in solution, micelles, sheets, vesicles, and fibrils that form hydrogels, as well as emulsions upon mixture with oils. By example, we have developed antimicrobial wash solutions, antimicrobial hydrogels and antimicrobial emulsions. All of these preparations can be applied to wounds, other tissues or other various surfaces. The directed molecular self-assembly of this invention determines chemical and biological characteristics, including hierarchical structure. It differs from the self-association of various random-sequence synthetic copolypeptides, which is based on non-uniform distribution of hydrophilic and hydrophobic residues, and typically results in irregular and ill-defined materials.

Preferred embodiments may also consider certain qualities that can impact the overall efficacy and toxicity in human or animal disease, including but not limited to the prevention and treatment of wound infections or other infectious diseases. These characteristics include, but are not limited to, fluidity (enabling ease of application), tissue coverage, duration of antimicrobial bioactivity, biocompatibility, degradation, biodistribution, and effects on inflammatory response, tissue repair, angiogenesis, hemostasis, immunogenicity and other. In certain medical settings (e.g., surgical or traumatic wounds), efficacy and toxicity may depend substantially on interactions of the synthetic copolypeptides with tissues. Certain advantages may be derived from synthetic copolypeptides that easily precipitate onto and/or directly bind to damaged tissues where they may provide a local, concentrated antimicrobial activity. Overall efficacy and safety in human or animal diseases will depend on the specific disease and the general condition of the patient. It is anticipated that in vivo bioactivities will depend substantially on formulation and hierarchical structure and that in vivo activity may not be fully revealed by in vitro testing.

DESCRIPTION OF THE FIGURES

FIG. 33 is a table (Table 1) of polypeptide synthetic data where $^a$=$M_n$ and PDI is determined using gel permeation chromatography (GPC) of the first segment, poly($N_\epsilon$-CBZ-L-lysine); compositions were calculated using: $^b$=GPC and $^1$H-NMR or $^c$=$^1$H-NMR in d-TFA. $^d$=Synthesized by guanylation of $K_{55}$(rac-L)$_{20}$;

FIG. 34 is a table (Table 2) of minimum contact time (min.) for 99.99% growth inhibition of E. coli 11229 and E. coli O157:H7, at copolypeptide concentration of 100 μg/mL;

FIG. 35 is a table (Table 3) showing minimum inhibitory concentration (MIC) of copolypeptides against various microbes including food-related microbes FIG. 38 is a table (Table 4) showing log reduction against Influenza A (enveloped virus) by copolypeptides at 1 mg/ml concentration after 30 sec of contact time;

FIG. 37 is a table (Table 5) showing minimum inhibitory concentration (MIC) of copolypeptides formulated as emulsions against B. subtilis endospores;

FIG. 38 is a table (Table 6) showing in vitro cytotoxicity in human keratinocytes, of copolypeptides formulated as solutions or emulsions, at concentration of 100 μg/ml; and FIG. 39 is a table (Table 7) showing thromboelastography (TEG) parameters for copolypeptides at concentration of 10 μg/mL; *Values were significantly different (p<0.05) than untreated controls.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide synthetic copolypeptides with high antimicrobial activity and low toxicity.

Figure 1:
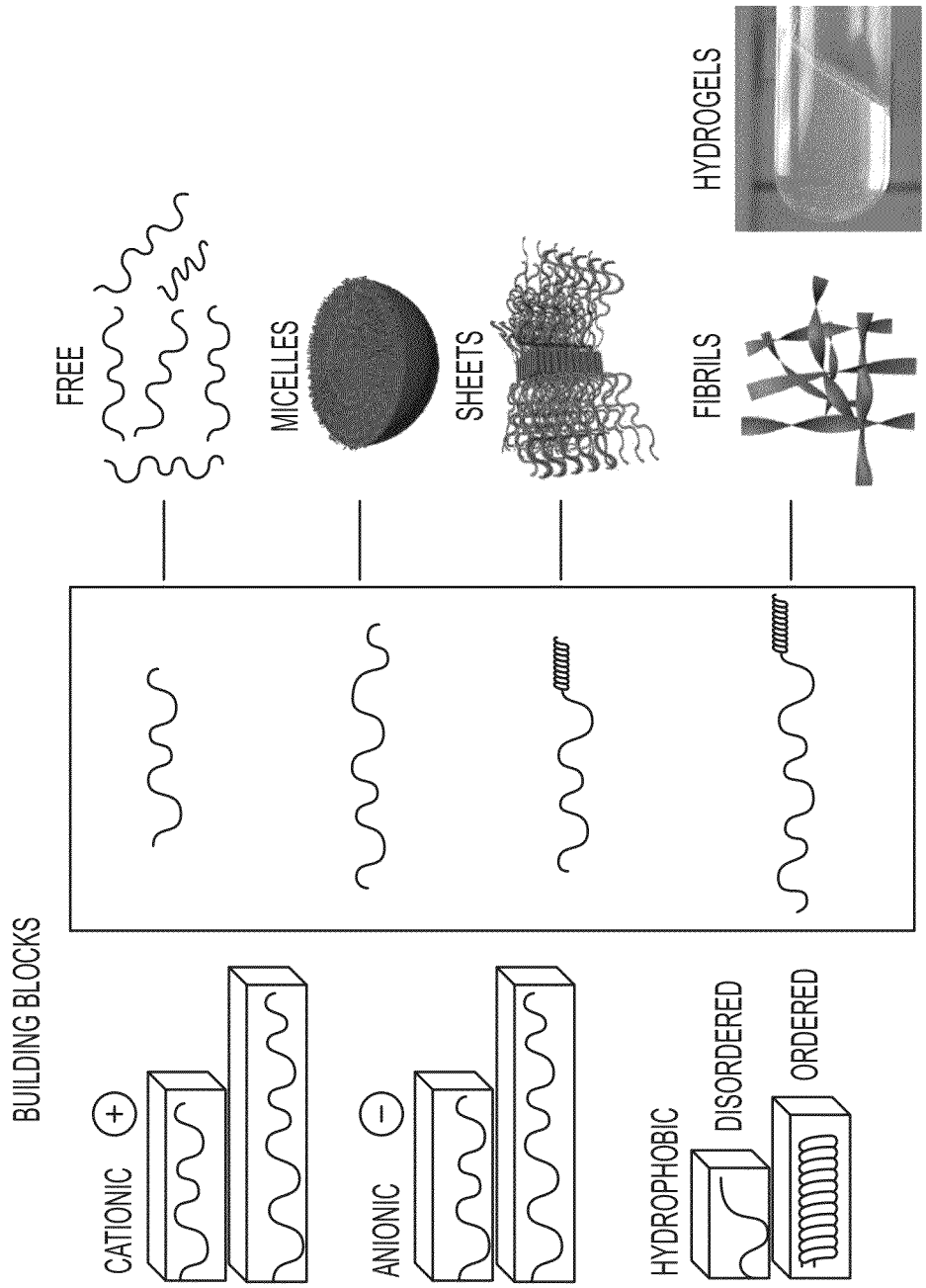
FIG. 1 is a diagram showing the variety of molecular building blocks that can be used to construct copolypeptides.
Figure 2:
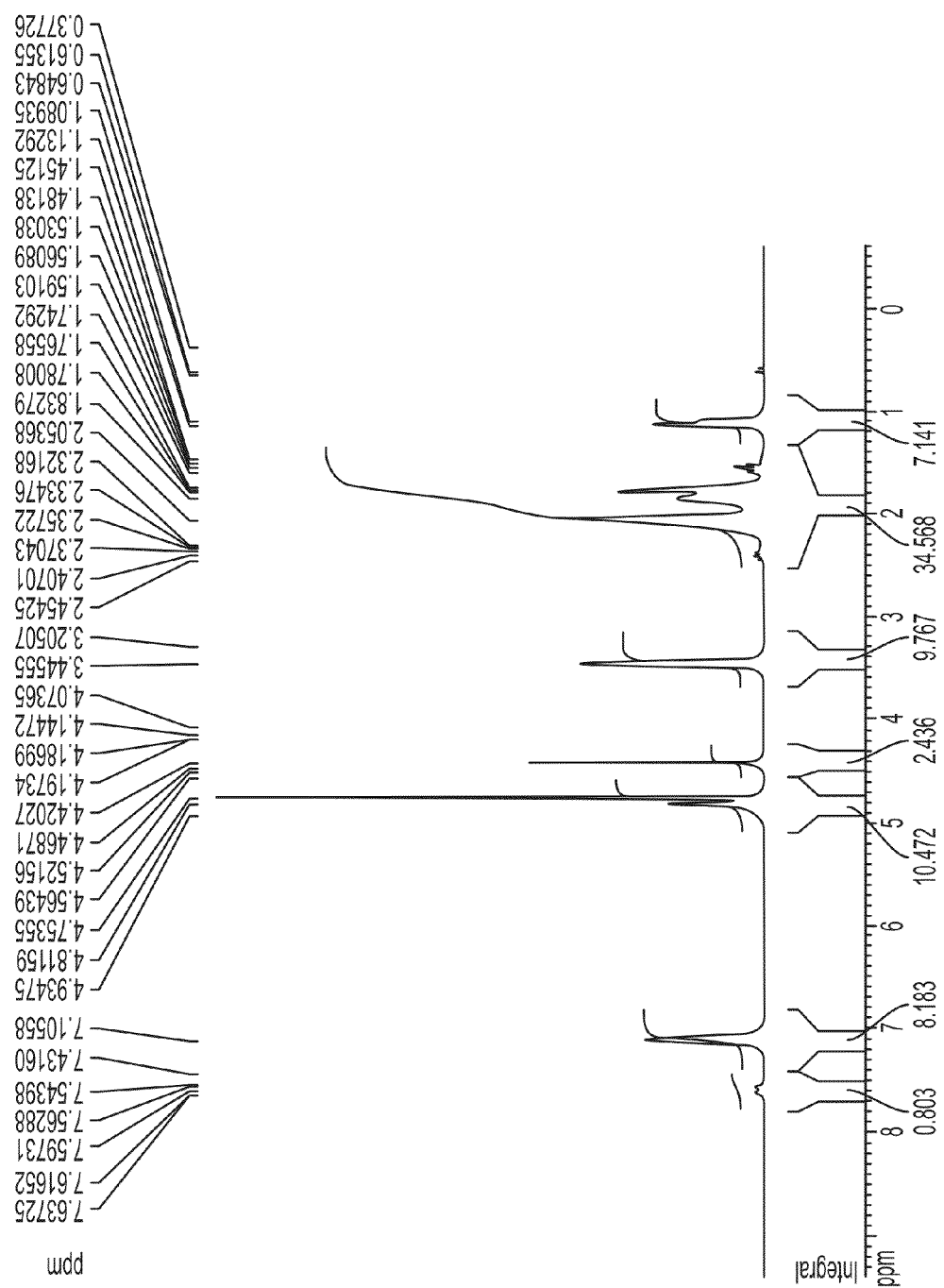
FIG. 2 is $^1$H-NMR of $K_{55}$(rac-L)$_{20}$ block copolypeptide in d-TFA.
Figure 3:
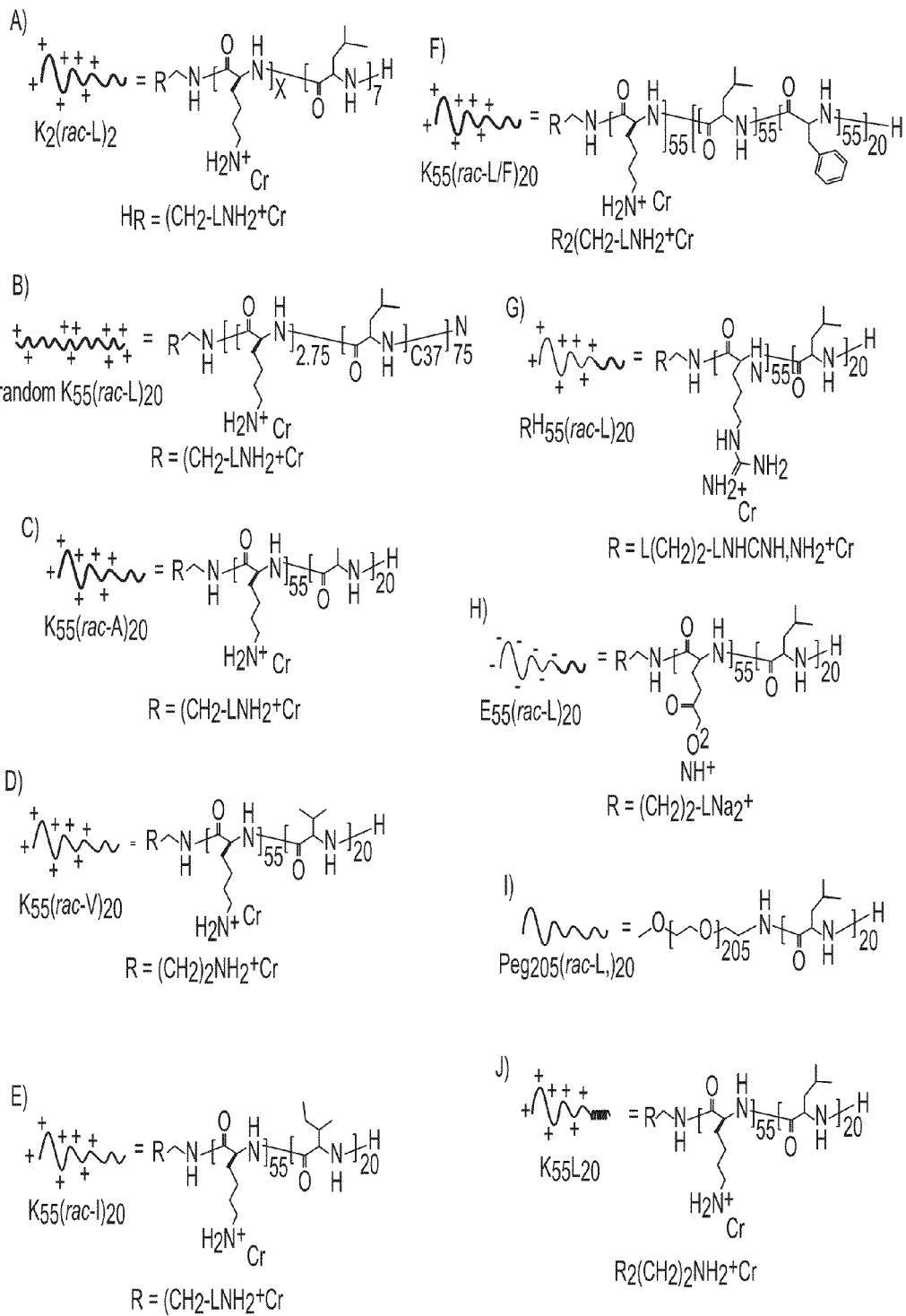
FIG. 3 is a diagram showing the structures of selected antimicrobial block copolypeptides: A) $K_x$(rac-L)$_y$; B) random $K_{55}$(rac-L)$_{20}$; C) $K_{56}$(rac-A)$_{20}$, D) $K_{55}$(V)$_{20}$; E) $K_{55}$(rac-V)$_{20}$; F) $K_{55}$(rac-L/F)$_{20}$; G) $R^H_{55}$(rac-L)$_{20}$; $E_{64}$/rac-L)$_{20}$; I) $PEG_{205}$(rac-L)$_{20}$; and J) $K_{50}L_{20}$.
Figure 4:
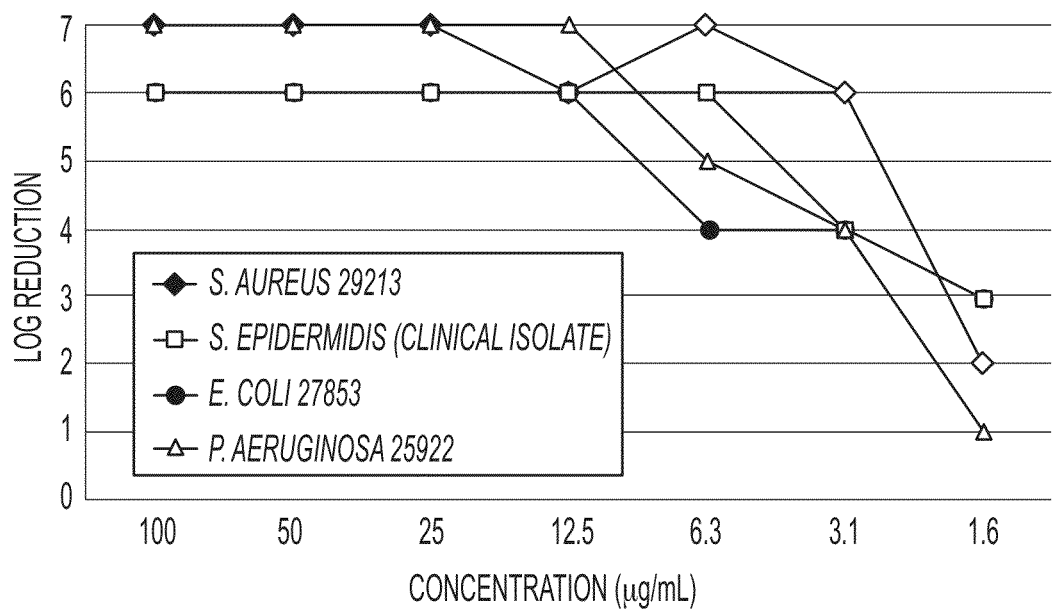
FIG. 4 shows the antimicrobial activity of $K_{55}$(rac-L)$_{20}$ block copolypeptide against *S. aureus, S. epidermidis, E. coli*, and *P. aeruginosa*; $K_{55}$(rac-L)$_{20}$ was incubated with bacteria for 30 min prior to plating for growth.

Antimicrobial copolypeptide compositions of this invention may contain one or more cationic amino acids (e.g. lysine, arginine, homoarginine, omithine) and one or more hydrophobic amino acids (e.g. leucine, valine, isoleucine, phenylalanine, alanine) arranged in blocks (FIGS. 1-3, FIG. 33 (Table 1)). Polycationic amphiphilic polypeptides (e.g., containing amine groups that are protonated at neutral pH, peralkylated ammoniums, or guanidiniums) display high antimicrobial activity. For example, as depicted in FIG. 4, we have demonstrated that a synthetic copolypeptide consisting of a block of 55 lysines followed by a block of 20 D and L (racemic) leucines ($K_{55}(rac-L)_{20}$) has substantial antimicrobial activity against *S. aureus* (Gram-positive), *S. epidermidis* (Gram-positive), *E. coli* (Gram-negative) and *P. aeruginosa* (Gram-negative). We have also demonstrated activity against several other bacterial and fungal organisms (see below). Multiple other synthetic copolypeptides have been synthesized (FIG. 33 (Table 1)) and show substantial antimicrobial activity. By contrast, at neutral pH (~7) polyanionic polypeptides (e.g. $E_{54}(rac-L)_{20}$) display low antimicrobial activity.

Figure 5:
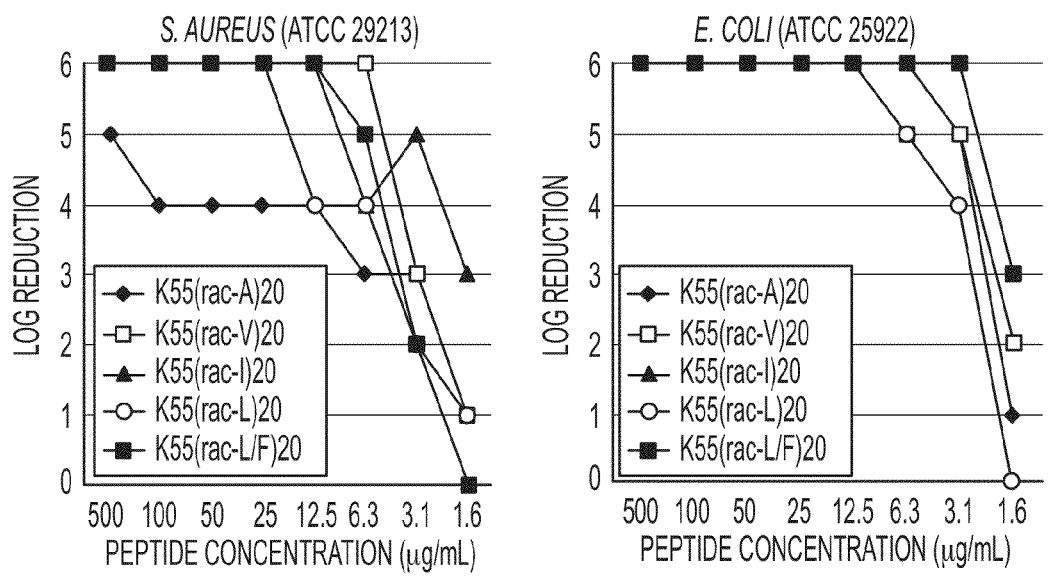
FIG. 5 shows the antimicrobial activity against *S. aureus* and *E. coli*, of copolypeptides with varying content of hydrophobic amino acid residues.
Figure 6:
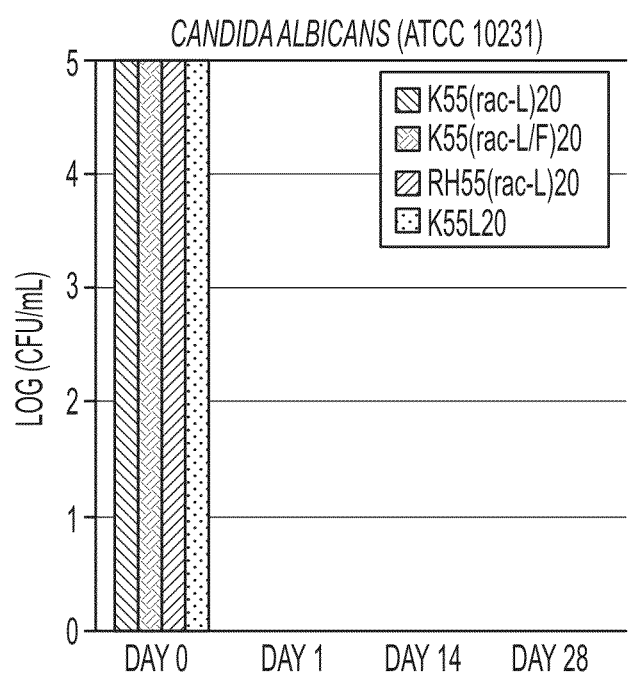
FIG. 6 shows the antimicrobial activity against *C. albicans* of copolypeptides at concentration of 100 μg/mL.
Figure 7:
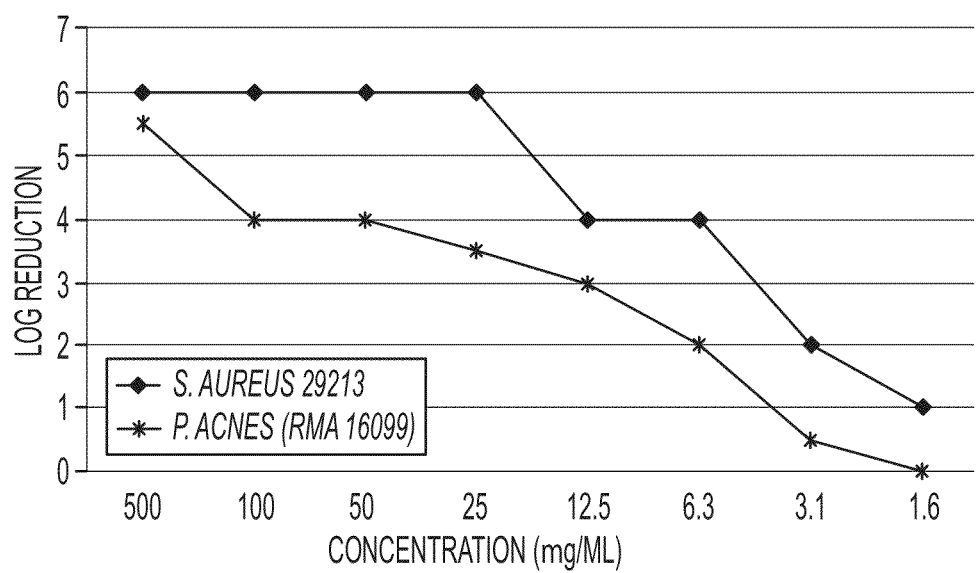
FIG. 7 shows the antimicrobial activity of $K_{55}$(rac-L)$_{20}$ block copolypeptide against *S. aureus* and *Propionibacterium acnes* (*P. acnes*); $K_{55}$(rac-L)$_{20}$ was incubated with bacteria for 30 min prior to plating for growth.

As depicted in FIG. 5, diblock synthetic copolypeptides based on cationic amino acid lysine and other hydrophobic amino acids demonstrate strong antimicrobial activity. In other studies, we demonstrated that partial guanylation of lysine residues resulted in high antimicrobial activity, for example $X_{55}(rac-L)_{20}$ for X=K/$R^H$ (homo-arginine) achieved high antimicrobial activity. Varying the hydrophobic amino acid composition, while keeping all other properties constant, also maintained high in vitro antimicrobial activity (FIG. 5). Specifically, poly(L-lysine-HCl)$_{55}$-bock-poly(racemic-hydrophobic amino acid)$_{20}$, $K_{55}(rac-X)_{20}$, for X=Alanine (A), Isoleucine (I), Leucine/Phenylalanine (L/F), or Valine (V), at very low concentration (10 μg/ml), achieved maximum observable (6-log) reduction of bacterial counts for both a Gram-positive (*S. aureus*) and a Gram-negative (*E. coli*) bacteria. Selected copolypeptides were also shown to be quite effective against other microbes including *E. coli* O157:H7, as well as other food-borne pathogens, and even against certain endospore forms of microbes (FIGS. 34 and 35 (Tables 2 and 3)). These compounds were also shown to be effective against certain fungal organisms as depicted for *Candida albicans* in FIG. 6. As depicted in FIG. 7, certain microbial organisms (e.g., *P. acnes*) may be less sensitive to certain copolypeptides than other microorganisms (e.g., *S. aureus*). Solution phase copolypeptides also demonstrated antiviral activity against H1N1 influenza virus (FIG. 36 (Table 4)). In this experiment, it was noted that the $R^H$/K (partially guanylated lysine) diblock copolypeptide were particularly active.

Figure 8:
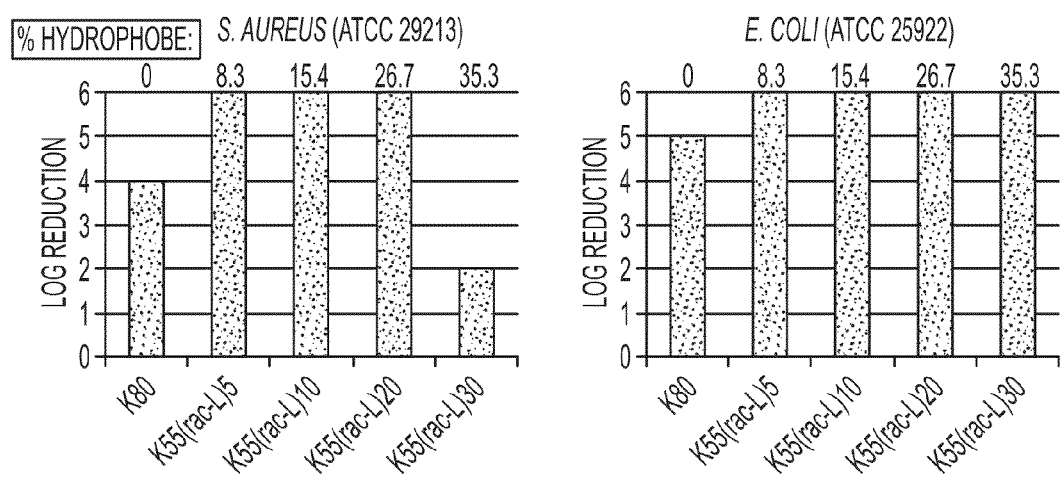
FIG. 8 show the antimicrobial activity against *S. aureus* and *E. coli*, of copolypeptides with varying sizes of block hydrophobic domains at peptide concentration of 10 μg/mL.
Figure 9:
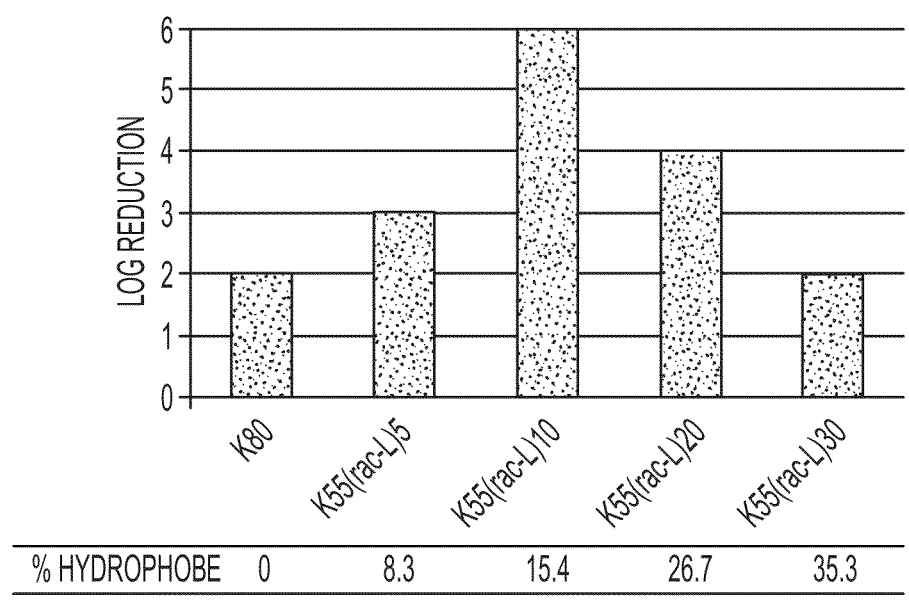
FIG. 9 shows the antimicrobial activity against *P. acnes*, of copolypeptides with varying sizes of hydrophobic domains at peptide concentration of 10 μg/mL.

In these block copolypeptides, we also demonstrated high antimicrobial activity when varying the length of the hydrophobic block (FIGS. 8 and 9). Unexpectedly, we demonstrated high antimicrobial activity in several series of synthetic block copolypeptides, including block copolypeptides with hydrophobe content below 40%. Even molecules with a block of as few as 5 or 10 hydrophobic leucine amino acids demonstrated good antimicrobial activity when constructed with a block of 55 cationic lysine amino acids.

Figure 10:
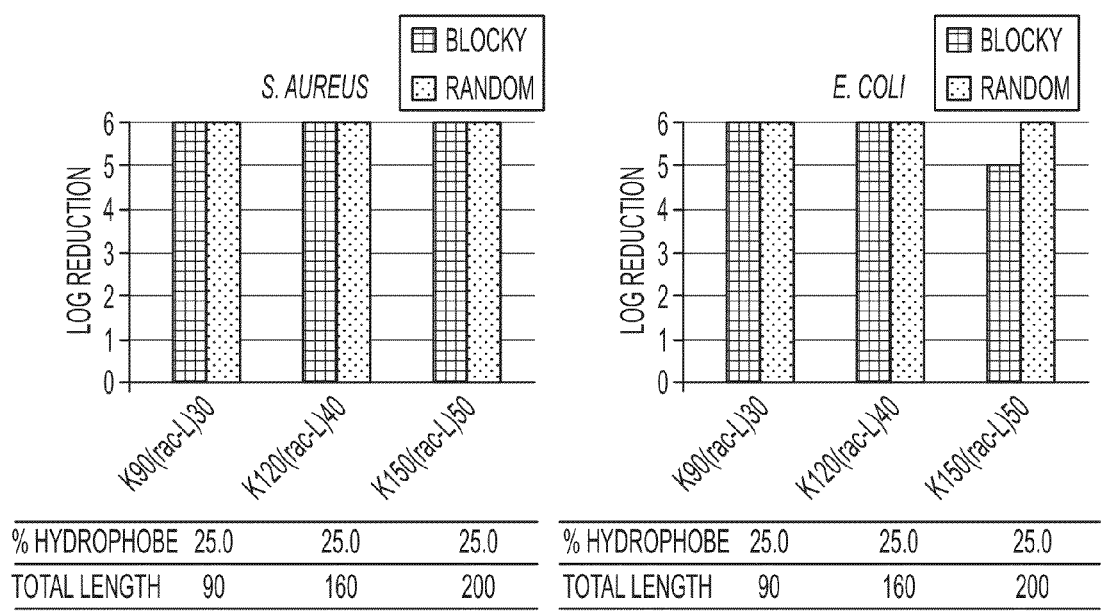
FIG. 10 shows the antimicrobial activity against *S. aureus* and *E. coli*, of copolypeptides formulated with blocky or random spatial distribution of monomers at peptide concentration of 10 ug/mL.

In separate studies we demonstrated that blocky copolypeptides with long hydrophilic blocks (i.e. longer than K90) were effective as antimicrobials (FIG. 10). In addition, we demonstrated that random synthetic copolypeptides of longer length (greater than 100 amino acid residues) were very effective antimicrobial agents. This was true for compounds of varying hydrophobe content.

In separate in vitro studies, we demonstrated that block-sequence copolypeptides in solution were less cytotoxic than random-sequence copolypeptides of similar composition. For example, we found that a blocky sequence $K_{55}L_{20}$ in solution decreased cell viability of mouse keratinocytes by 50% ($EC_{50}$), at 47.4 ug/ml, whereas a synthetic copolypeptide of similar composition in random sequence had an $EC_{50}$ of 21.0 ug/ml in solution. Similarly, block-sequence $K_{55}(rac-L)_{20}$ in solution was found to be less cytotoxic than random-sequence $K_{55}(rac-L)_{20}$ in solution. As described below, a variety of synthetic copolypeptides were found to be antimicrobial in emulsion preparations. In these preparations, block sequence synthetic copolypeptides were also found to be less cytotoxic (lower $EC_{50}$) than random sequence copolypeptides, even though, the block sequence copolypeptide stabilized emulsions typically demonstrated equivalent (and sometimes higher) antimicrobial activity.

Figure 11:
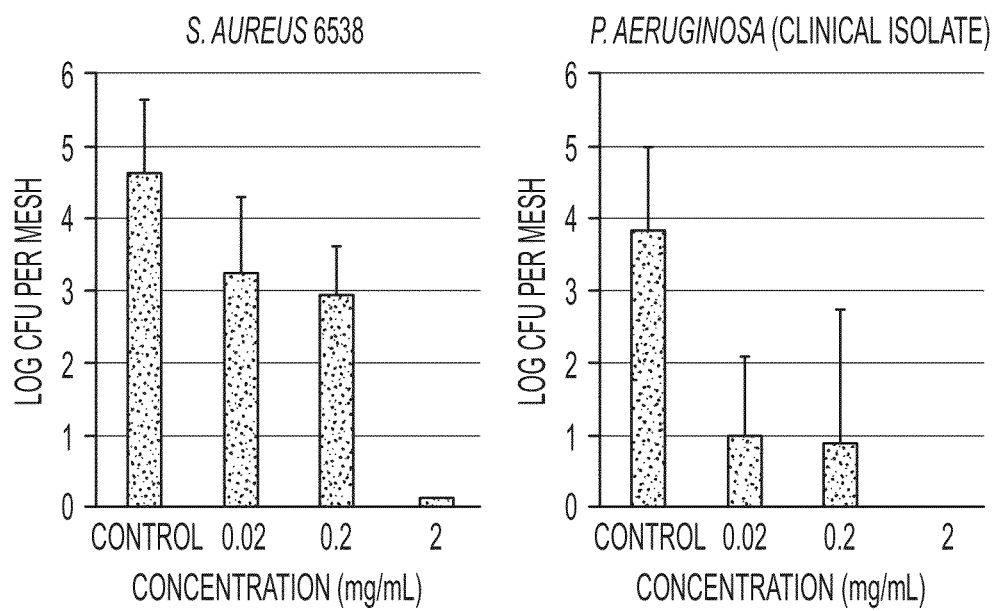
FIG. 11 shows the antimicrobial activity of $K_{55}$(rac-L)$_{20}$ in a rodent model; a polypropylene mesh pre-soaked with PBS or $K_{55}$(rac-L)$_{20}$ was inserted subcutaneously in rats, with additional copolypeptide, and an inoculum of either 10$^6$ *S. aureus* 6538 or *P. aeruginosa* (Clinical Pig Isolate) was added; after two days, the implanted mesh was plated for bacterial enumeration.
Figure 12:
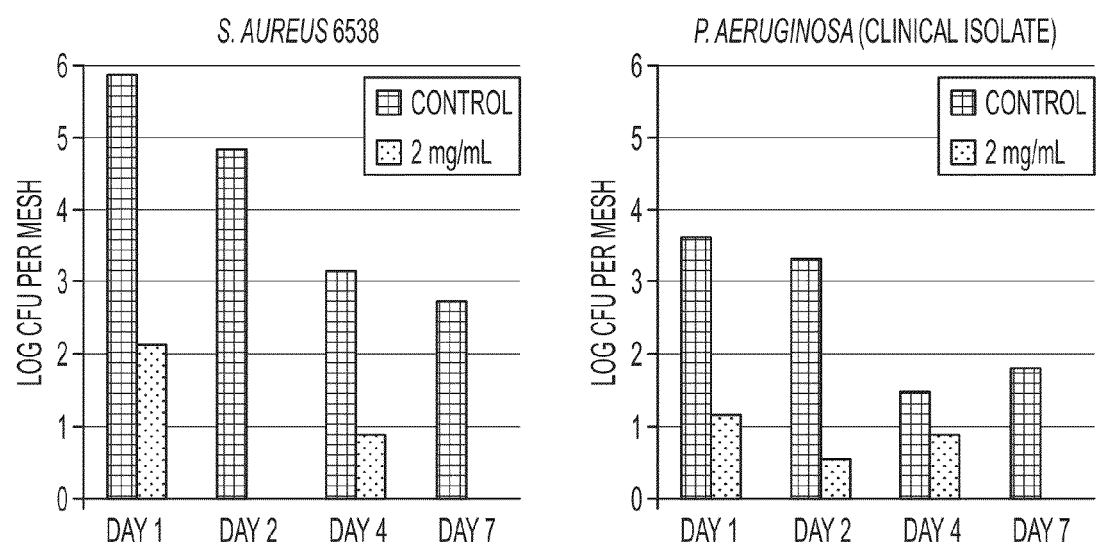
FIG. 12 shows the antimicrobial activity of $K_{55}$(rac-L)$_{20}$ in a rodent model; a polypropylene mesh pre-soaked with PBS or $K_{55}$(rac-L)$_{20}$ was inserted subcutaneously in rats, with additional copolypeptide, and an inoculum of either 10$^6$ *S. aureus* 6538 or *P. aeruginosa* (Clinical Pig Isolate) was added; at various timepoints, the implanted mesh was plated for bacterial enumeration.
Figure 13:
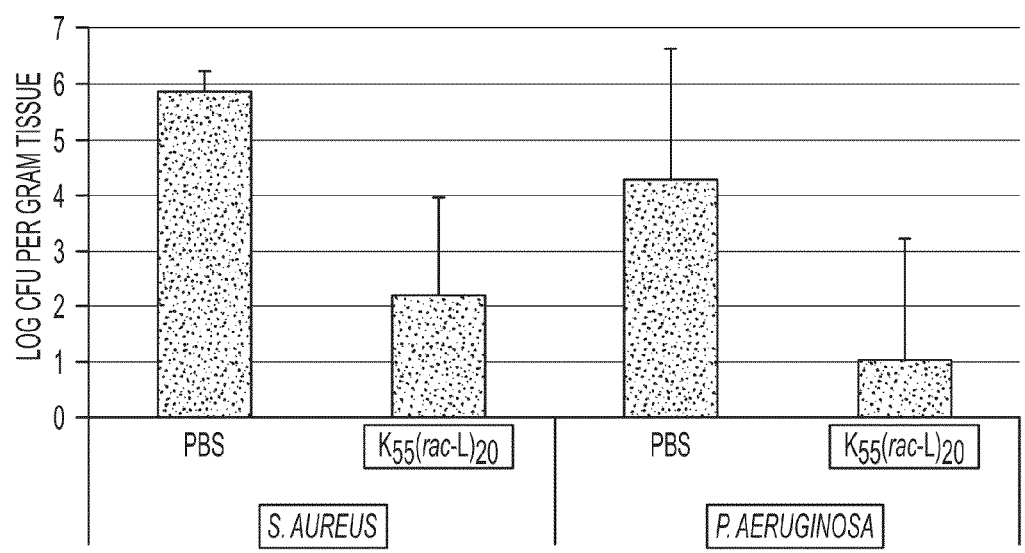
FIG. 13 shows the antimicrobial activity of $K_{55}$(rac-L)$_{20}$ in a rodent model; a polypropylene mesh pre-soaked with PBS or 2 mg/ml $K_{55}$(rac-L)$_{20}$ was inserted subcutaneously in rats, with additional copolypeptide, and a inoculum of either 10$^6$ *S. aureus* 6538 or *P. aeruginosa* (Clinical Pig Isolate) was added; after two days, the surrounding tissue was plated for bacterial enumeration.

A solution phase block-sequence synthetic copolypeptide $K_{55}(rac-L)_{20}$ was also shown to be effective in a rodent model of prevention of wound infection (FIGS. 11-13). We have demonstrated reductions in bacterial populations in an infection prevention model against *S. aureus* and *P. aeruginosa*. Consistent, concentration-dependent reductions were observed—typically, 1-3 log reduction at 20 μg/ml of copolypeptide, $K_{55}(rac-L)_{20}$, and complete (or near complete) reduction at 2 mg/ml. These studies indicate that copolypeptide formulations remain active when exposed to complex biological fluid. Notably, copolypeptides could be formulated as either aqueous suspensions or mixed with oil and water and self-assembled into nanoemulsions; certain antimicrobial copolypeptides are effective surfactants (see below for emulsions).

Figure 14:
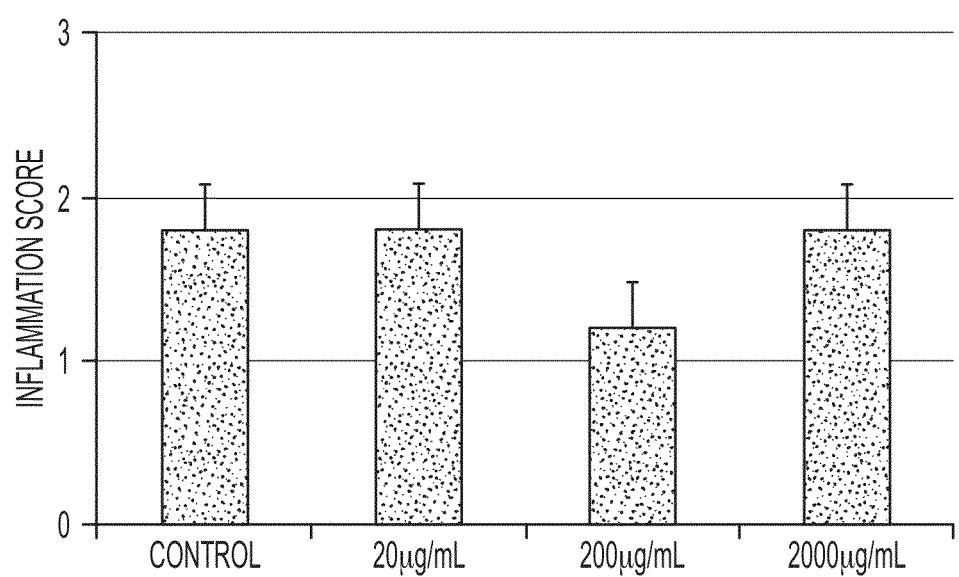
FIG. 14 shows the results of assaying inflammation in a rodent model; a polypropylene mesh pre-soaked with $K_{55}$(rac-L)$_{20}$ copolypeptide was inserted subcutaneously in rats, with additional copolypeptide, and an inoculum of $10^6$ S. aureus 6538 was added; after 48 hrs, tissue was analyzed by histology for inflammation: 0=normal, 1=mild, 2=moderate, 3=severe.

Importantly, the block-sequence synthetic copolypeptides $K_{55}(rac-L)_{20}$ in solution did not appear to be irritating to open wounds. As depicted in FIG. 14, histopathological evidence suggested that inflammation was at or below the level of control treatments.

Figure 15:
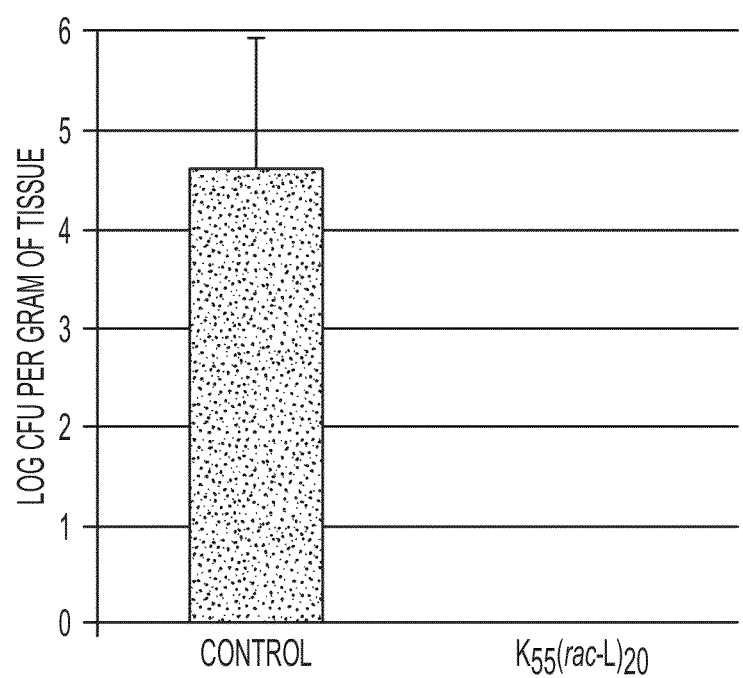
FIG. 15 shows the antimicrobial activity of $K_{55}$(rac-L)$_{20}$ in a porcine model; $K_{55}$(rac-L)$_{20}$ (10 mg/mL) was applied to wounds, and after four hrs, remaining material was aspirated and $10^7$ S. aureus 6538 was added to wounds; after 48 hrs, bacterial counts were assessed.
Figure 16:
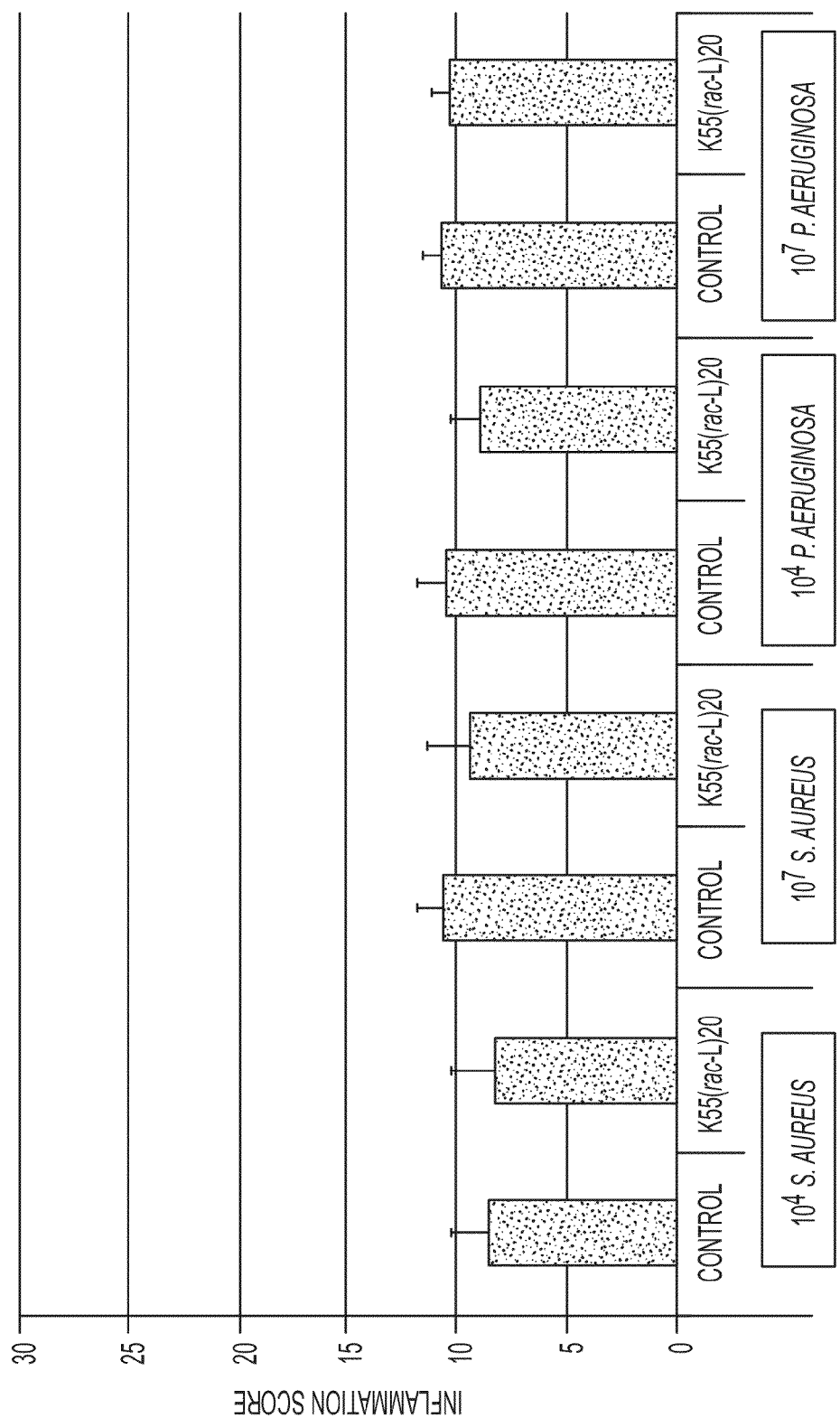
FIG. 16 shows the result of assaying for inflammation in a porcine model; $K_{55}$(rac-L)$_{20}$ (10 mg/mL) was applied to wounds, an after 30 mins, $10^4$ or $10^7$ S. aureus or P. aeruginosa was added to wounds; after 48 hrs, tissues were analyzed by histology for inflammation (including cell infiltration and necrosis)
Figure 17:
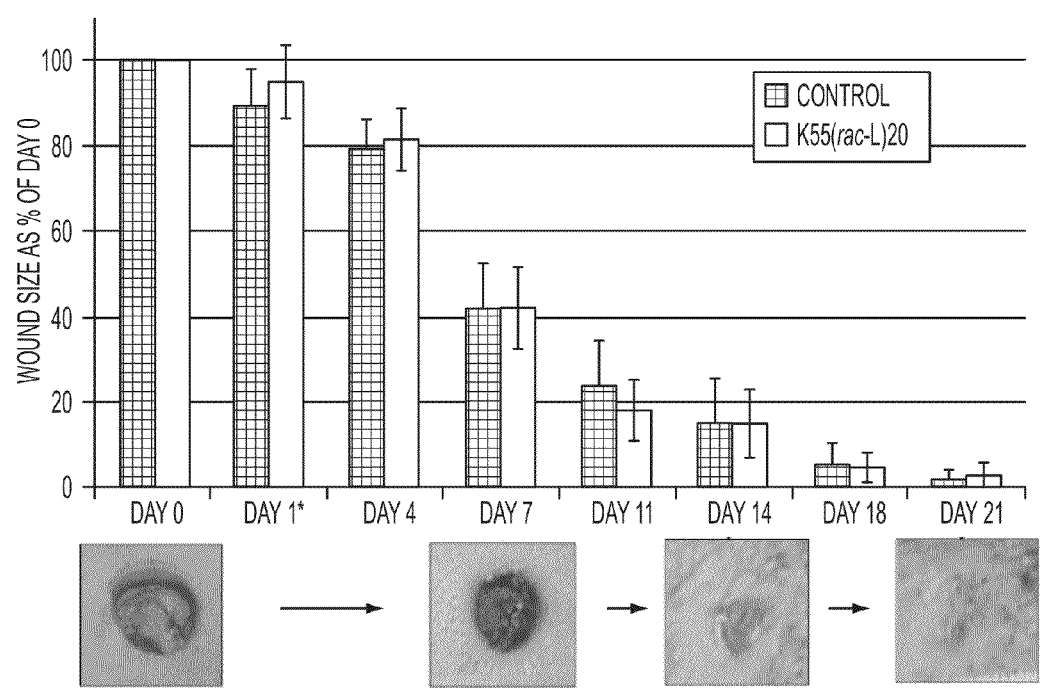
FIG. 17 shows wound healing in a porcine model in which wounds were treated with 500 μg/mL of $K_{55}$(rac-L)$_{20}$ and monitored over a 21 day period.

Solution phase antimicrobial copolypeptides were also found to be highly effective in a porcine infection prevention model. As depicted in FIG. 15, $K_{55}(rac-L)_{20}$ solution applied to an open wound prior to inoculation with *S. aureus* fully prevented microbial infection. In separate studies, copolypeptide $K_{55}(rac-L)_{20}$, where the hydrophobic block is racemic poly-D/L-leucine, exhibited excellent tissue biocompatibility in animal models. For example, in a two-day porcine open-wound study (FIG. 16), histological analysis (by a veterinary pathologist) showed "serocellular exudates and neutrophilic inflammation were mildly and minimally less severe, respectively," in $K_{55}(rac-L)_{20}$-treated animals versus controls. No differences were observed in mononuclear inflammation, edema, or hemorrhage. In a 21-day porcine wound healing study (non-infected), $K_{55}(rac-L)_{20}$-treated and control-treated wounds were found to be similar in inflammation, necrosis, and epithelial coverage by a veterinary pathologist (FIG. 17).

Antimicrobial Emulsions Based on Synthetic Copolypeptides.

Figure 18:
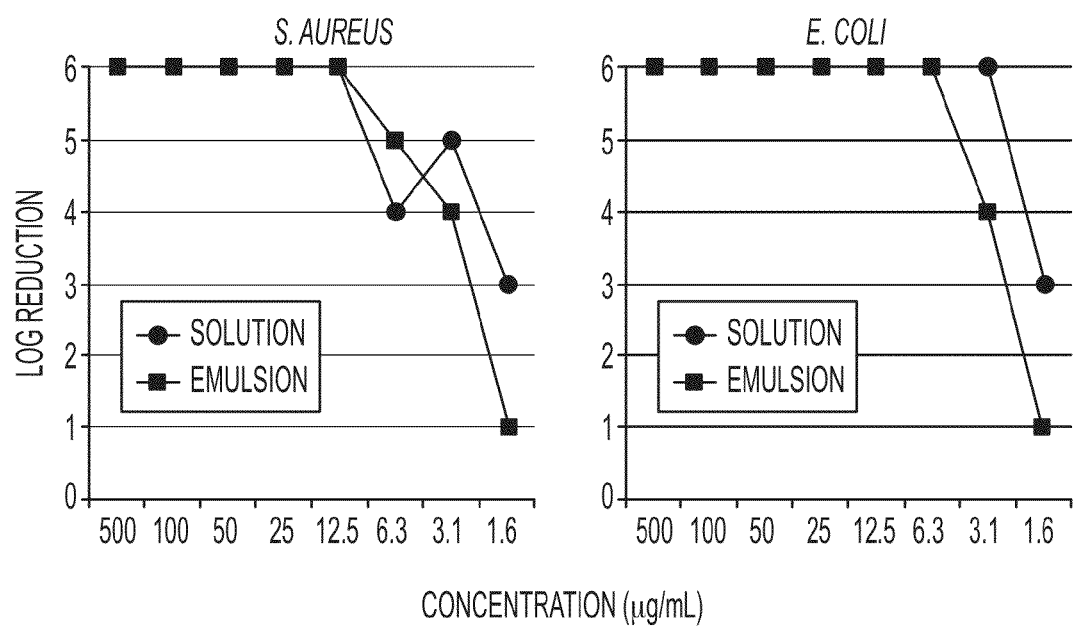
FIG. 18 shows antimicrobial activity against S. aureus and E. coli of $K_{55}$(rac-L)$_{20}$ block copolypeptides formulated as solutions or emulsions.
Figure 19:
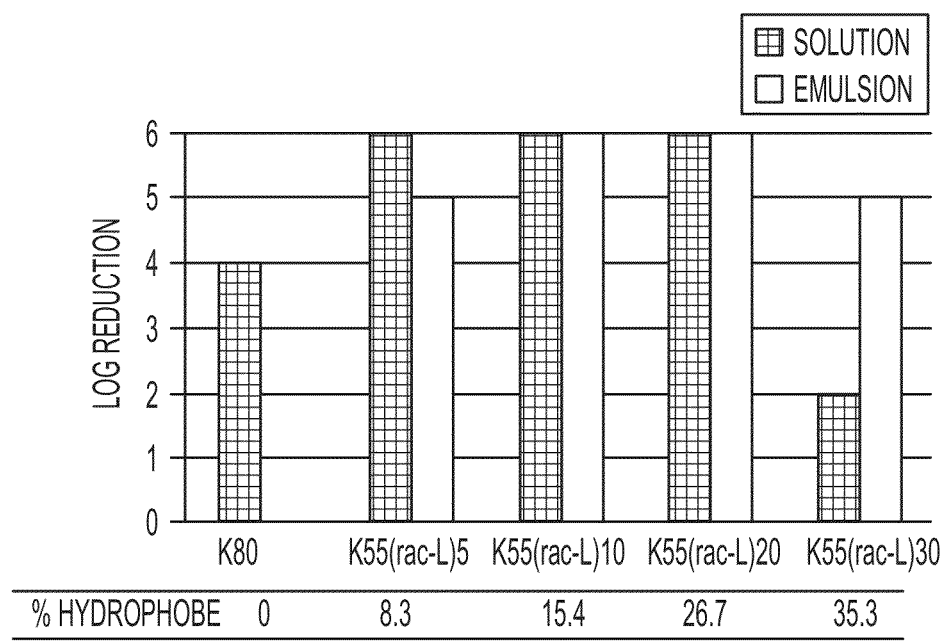
FIG. 19 shows antimicrobial activity against S. aureus, of copolypeptides formulated as either solutions or emulsions with varying sizes of hydrophobic domains at peptide concentration of 10 μg/mL.

These synthetic copolypeptides can be designed to be effective surfactants that may stabilize (and/or be displayed on) emulsions. We have demonstrated that a variety of synthetic copolypeptide-emulsion preparations are effective antibacterials in vitro (FIGS. 18 and 19). Notably, these antimicrobial emulsions were found to be active against *B. subtilis* endospores (FIG. 37 (Table 5)). As described above for solution phase copolypeptides, emulsion preparations demonstrated antiviral activity against H1N1 influenza virus (FIG. 36 (Table 4)), as well as against a non-enveloped bacteriophage.

Figure 20:
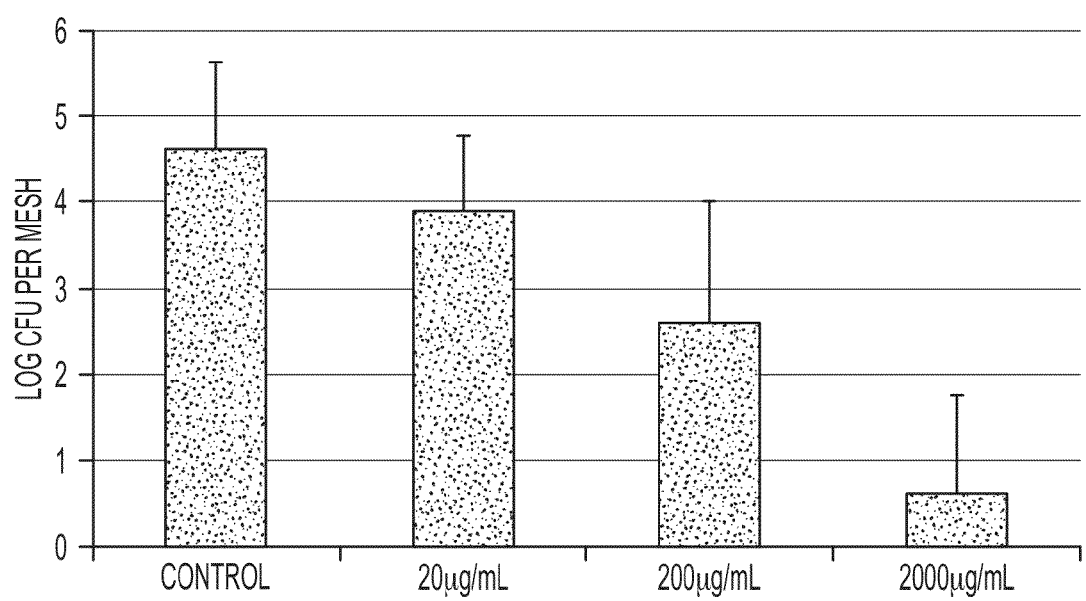
FIG. 20 shows the in vivo antimicrobial activity against S. aureus of $K_{55}$(rac-L)$_{20}$ copolypeptide formulated as an emulsion; a polypropylene mesh pre-soaked with copolypeptide was inserted subcutaneously in rats, with additional copolypeptide, and an inoculum of $10^6$ S. aureus 6538 was added; after 2 days, the implanted mesh was plated for bacterial enumeration.

Antimicrobial emulsions based on synthetic copolypeptides were also found to be effective in an infection prevention model in rodents (FIG. 20). We have demonstrated reductions in bacterial populations in an infection prevention model against *S. aureus*. Consistent, concentration-dependent reductions were observed—typically, 1-4 log reduction at 20 μg/ml of copolypeptide, $K_{55}(rac-L)_{20}$ based emulsions and complete (or near complete) reduction at 2 mg/ml. These studies indicate that copolypeptide emulsion formulations remain active when exposed to complex biological fluid.

Figure 21:
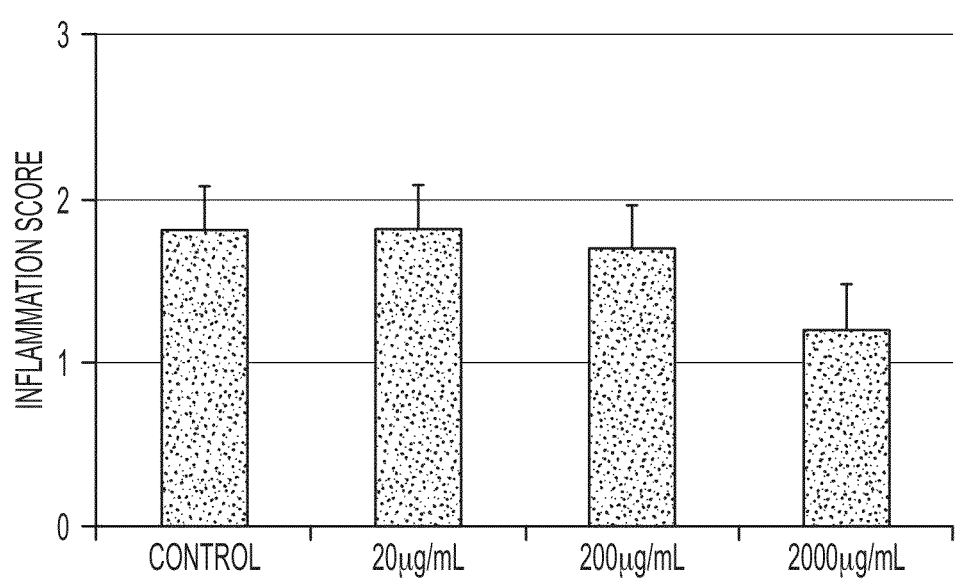
FIG. 21 show the results of assaying for inflammation in a rodent model; $K_{55}$(rac-L)$_{20}$ copolypeptide was formulated as an emulsion, and a polypropylene mesh pre-soaked with copolypeptide was inserted subcutaneously in rats, with additional copolypeptide; an inoculum of $10^6$ S. aureus 6538 was added, and after 48 hrs, tissue was analyzed by histology for inflammation: 0=normal, 1 mild, 2=moderate, 3=severe.
Figure 22:
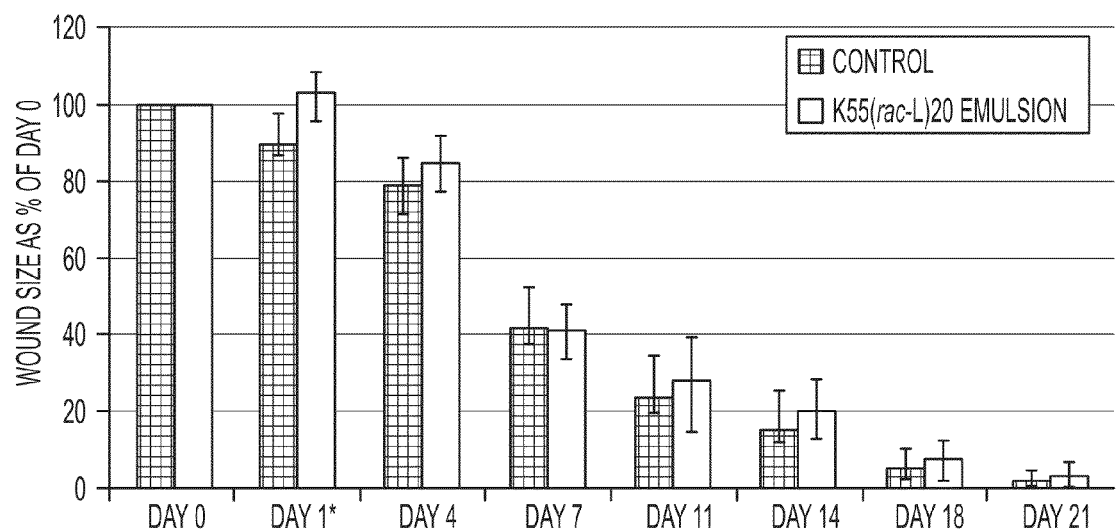
FIG. 22 shows wound healing in a porcine model in which wounds were treated with 500 μg/mL of $K_{55}$(rac-L)$_{20}$ formulated as an emulsion and monitored over a 21 day period.

These antimicrobial emulsions appear to be well tolerated in wounds and did not result in increased inflammation over control treatments, as assessed by histological examination (FIG. 21). In addition, these antimicrobial emulsions were found to be well tolerated in a 21-day porcine model of wound healing (non-infected) (FIG. 22).

Further studies suggested that antimicrobial synthetic copolypeptide emulsions have less cytotoxicity in vitro (FIG. 38 (Table 6)). In other studies, this observation was consistent across multiple synthetic copolypeptides including $K_{55}$(rac-L)$_{20}$, $K_{55}L_{20}$, $K_{55}$(rac-L/F)$_{20}$. Taken together, these data indicate that the arrangement of synthetic block-sequence copolypeptides into the hierarchical structures of emulsions and nanoemulsions may improve antimicrobial activity, reduce mammalian toxicity, or both.

Antimicrobial Hydrogels Based on Synthetic Copolypeptides.

Figure 23:
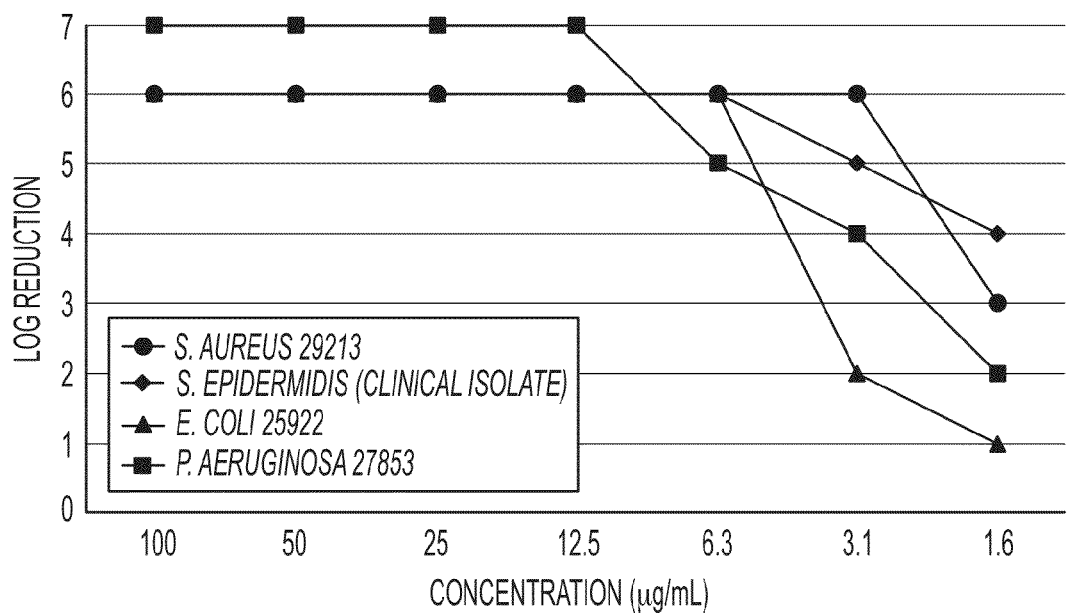
FIG. 23' shows the antimicrobial activity of $K_{180}L_{20}$ block copolypeptides. $K_{180}L_{20}$ was incubated with bacteria for 30 min prior to plating for growth.

This invention also describes block copolypeptides that self-assemble into fibrils that form antimicrobial hydrogels. As described below, $K_{180}L_{20}$, is a hydrogel-former and has demonstrated strong antimicrobial activity in vitro and effective prevention of microbial growth in studies in vivo. As depicted in FIG. 23, $K_{180}L_{20}$ demonstrated potent antimicrobial activity in vitro (5+ log reduction at 6.3 μg/mL) against Gram-positive (*S. aureus, S. epidermidis*) and Gram-negative (*E. coli, P. aeruginosa*) bacteria that are known to be important in wound infection. In time kill assays, $K_{180}L_{20}$ at 100 μg/mL showed more than 3 log reduction in 5 min against *S. epidermidis, E. coli*, and *P. aeruginosa*.

Figure 24:
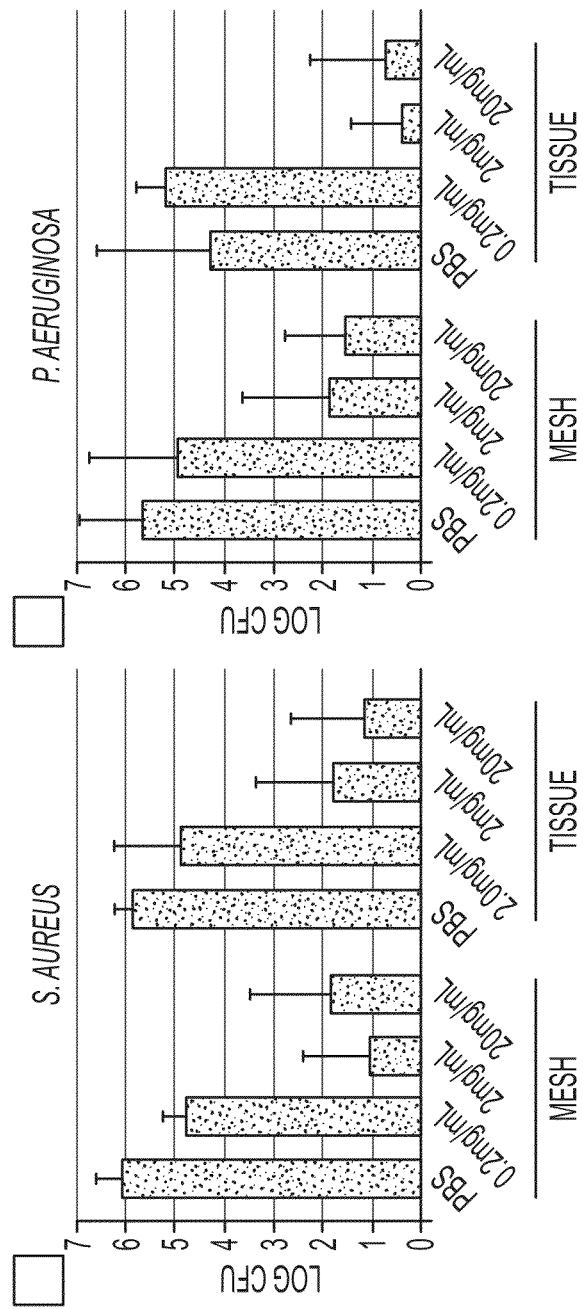
FIG. 24 shows the antimicrobial activity of $K_{180}L_{20}$ in a rodent model; a polypropylene mesh pre-soaked with PBS or $K_{180}L_{20}$ was inserted subcutaneously in rats, with additional copolypeptide; an inoculum of either $10^6$ S. aureus 6538 or P. aeruginosa (Clinical Pig Isolate) was added; after 48 hrs, the implanted mesh and surrounding tissue were plated for bacterial enumeration.
Figure 25:
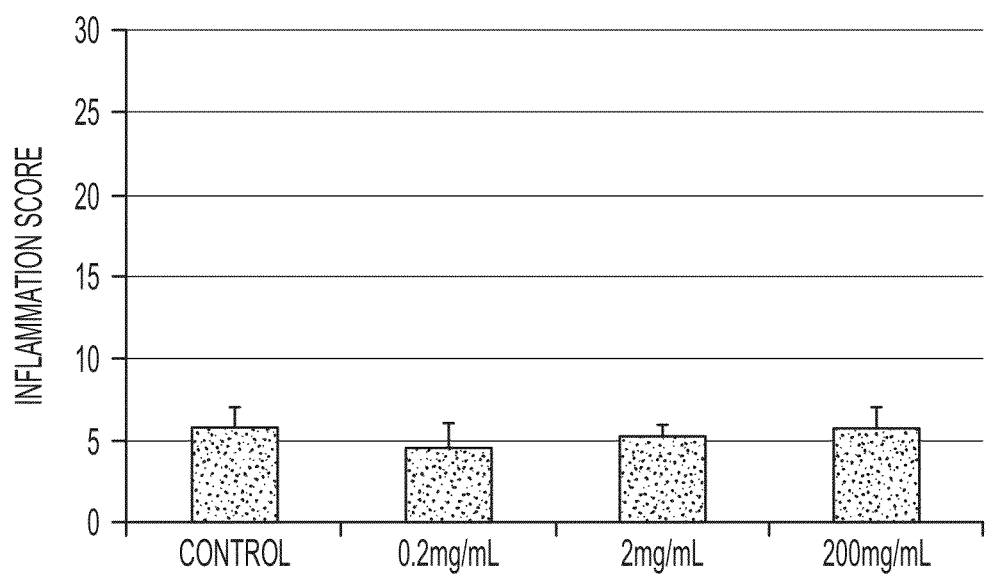
FIG. 25 shows the results of assaying inflammation in a rodent model; a polypropylene mesh pre-soaked with PBS or $K_{180}L_{20}$ copolypeptide was inserted subcutaneously in rats, with additional copolypeptide, and an inoculum of $10^6$ S. aureus 6538 was added; after 48 hrs, the surrounding tissue was analyzed by histology for inflammation (including cell infiltration and necrosis)

Other studies demonstrated that $K_{180}L_{20}$ block copolypeptides are antimicrobial in vivo. As depicted in FIG. 24, $K_{180}L_{20}$ was effective in inhibiting microbial growth in a rodent closed-wound model with foreign body. In this model, a mesh pre-soaked with phosphate buffered saline (PBS) or $K_{180}L_{20}$ was inserted subcutaneously into the dorsal cervical region of Sprague-Dawley rats, followed by $10^6$ *S. aureus* or *P. aeruginosa*. Additional PBS or $K_{180}L_{20}$ was added, wounds closed, and animals returned to cages for 48 hr. $K_{180}L_{20}$ (2 mg/ml and 20 mg/ml) substantially decreased the number of bacteria (both *S. aureus* and *P. aeruginosa*) cultured from the mesh and adjacent tissue. No enhanced inflammation was observed with this antimicrobial hydrogel in the rodent model of infection (FIG. 25).

Figure 26:
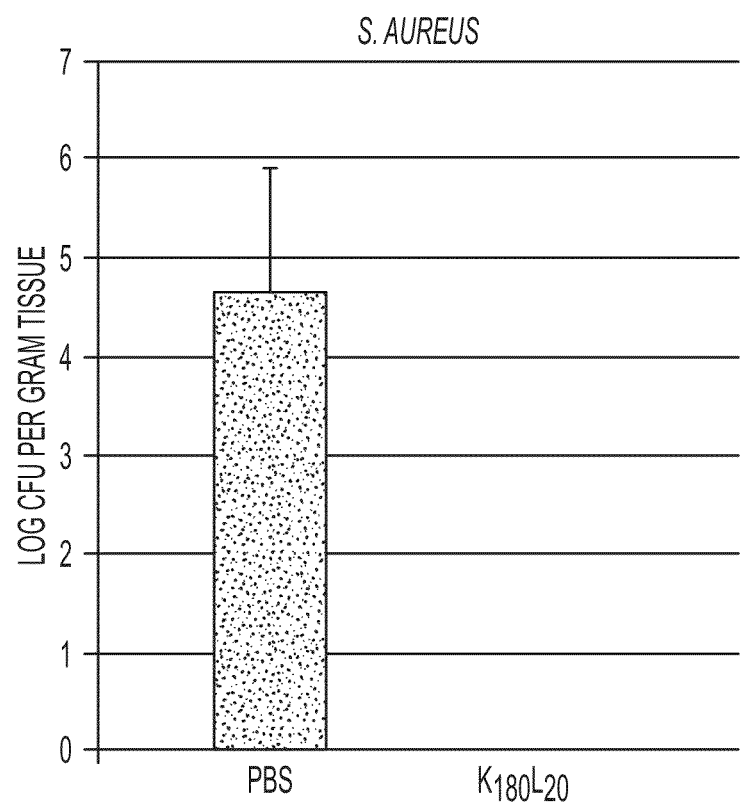
FIG. 26 shows the antimicrobial activity of $K_{180}L_{20}$ in a porcine model; $K_{180}L_{20}$ (40 mg/mL) was applied to wounds, and after 4 hrs, $10^7$ S. aureus 6538 was added to wounds; after 48 hrs, final bacterial counts were assessed.
Figure 27:
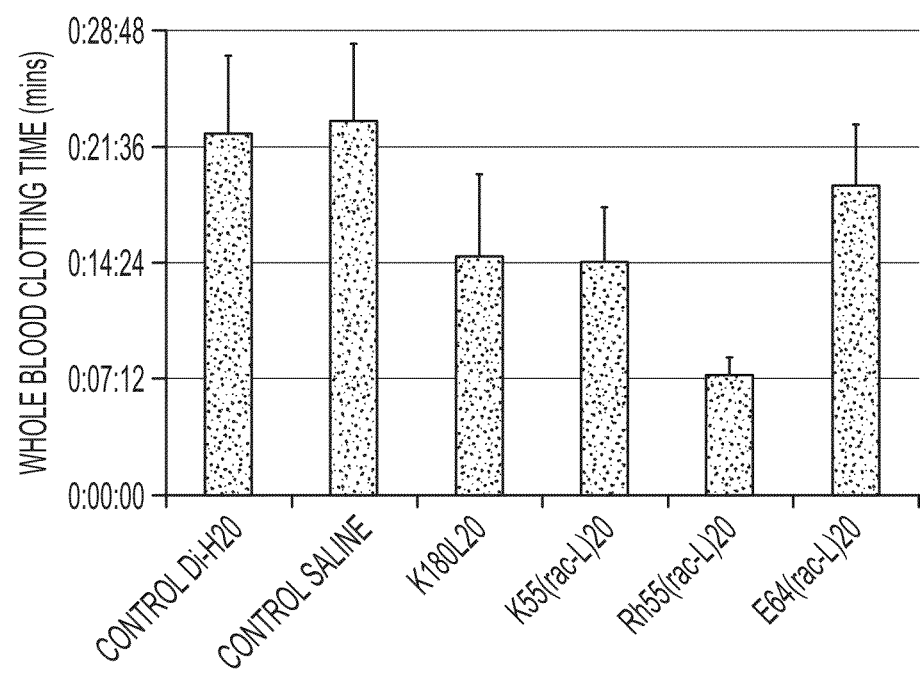
FIG. 27 show the effect of copolypeptides on clotting time of whole blood, at copolypeptide concentration of 10 μg/mL.
Figure 28:
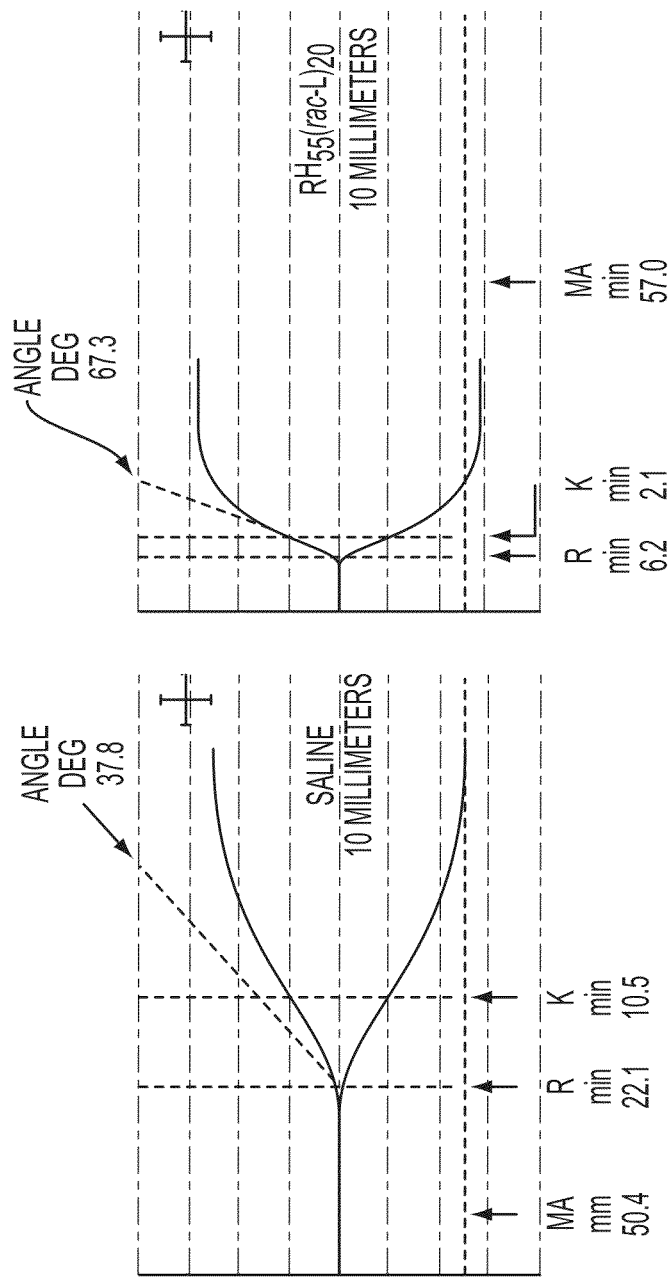
FIG. 28 shows the results of a thromboelastography (TEG) assay to measure effects of copolypeptides on blood clotting at copolypeptide concentration of 10 μg/mL; R time is latency time between placement of blood in TEG apparatus and initial increase in viscosity (measured by trace increase from 0-2 mm); R time corresponds to enzymatic activity of coagulation factors prior to ramp-up of cross-linking; K time corresponds to the amplitude increasing from 2-20 mm; alpha angle is the slope of the TEG tracing between R and the K times; alpha angle measures speed of clot development, and maximum amplitude (MA) is the highest trace and provides an absolute measure of clot strength.
Figure 29:
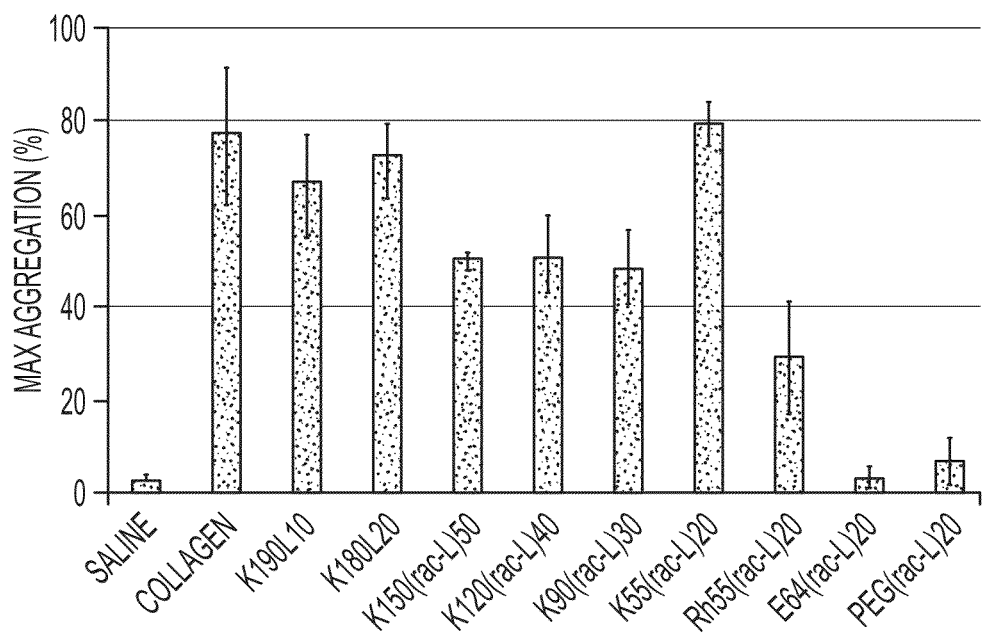
FIG. 29 shows the effect of copolypeptides on platelet aggregation in platelet-rich plasma with a copolypeptide concentration of 100 μg/mL.
Figure 30:
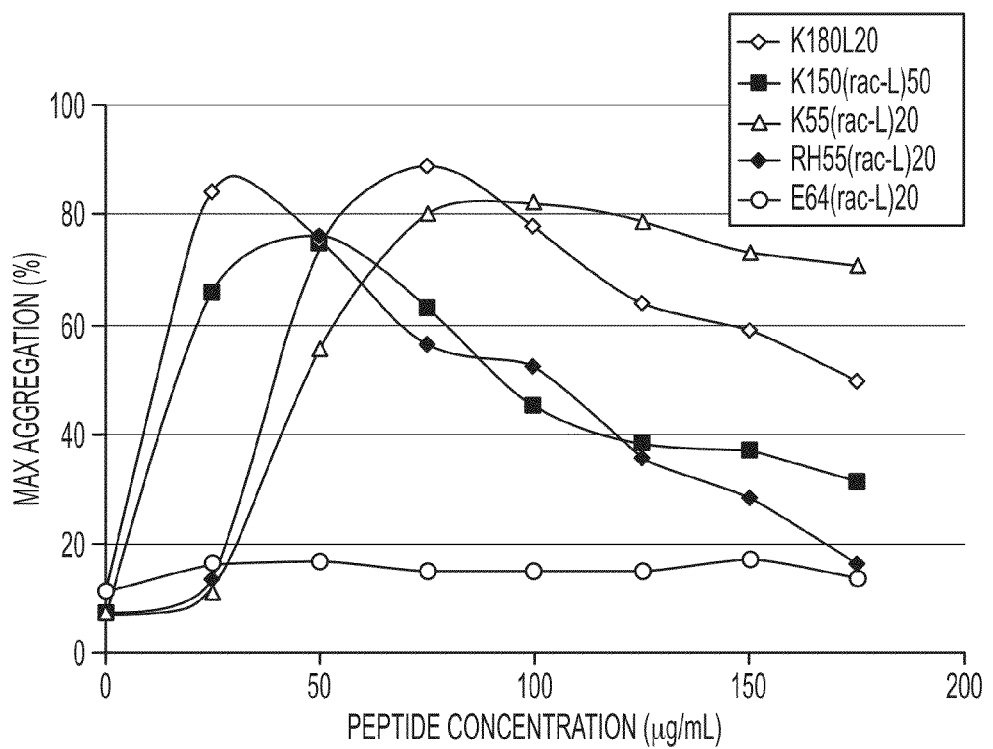
FIG. 30 show the effect of copolypeptides on platelet aggregation.
Figure 31:
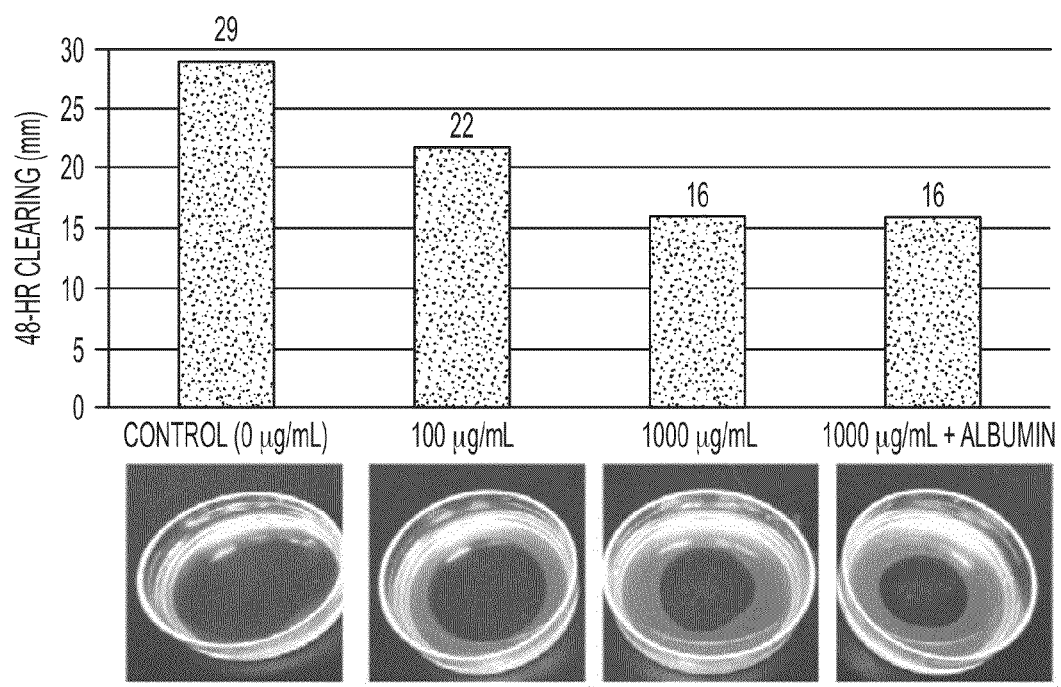
FIG. 31 shows a fibrin gel plate assay used to measure effects on fibrinolysis of $R^H{}_{55}$(rac-L)$_{20}$ copolypeptide at concentrations of 100, 1000 μg/ml and 1000 μg/ml with 1 mg/ml albumin.
Figure 32:
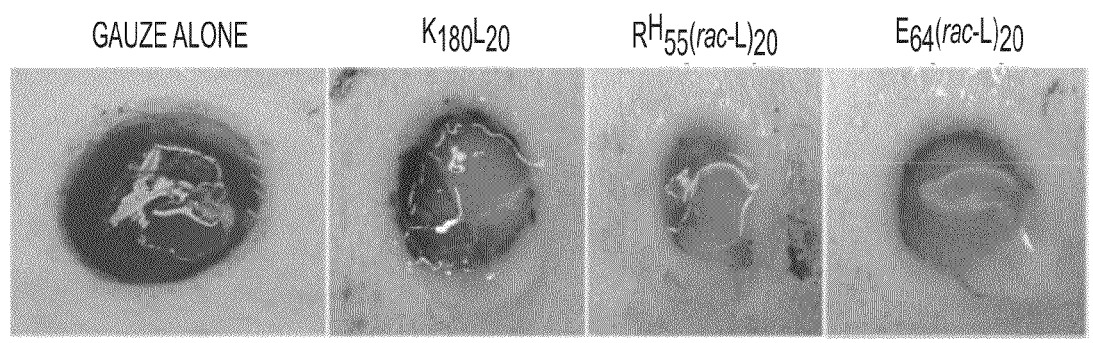
FIG. 32 shows images from porcine venous bleeding depicting 15 mm wounds at 5 min filled with PEG-based gels containing copolypeptides.

In a separate study, the hydrogel based on block-sequence copolypeptide $K_{180}L_{20}$ was effective in inhibiting *S. aureus* in a porcine open-wound model (FIG. 26). Full-thickness 1 cm diameter wounds were made in the dorsal and lateral thorax of a 25-35 kg Yorkshire-cross pig. $K_{180}L_{20}$ hydrogel (or control buffer) was applied, and after four hr, wounds were inoculated with *S. aureus*. Wounds were assessed after 48 hr for bacterial counts by standard microbiology methods. As depicted in FIG. 26, $K_{180}L_{20}$ hydrogel fully reduced *S. aureus* counts.

Block-sequence structure. In certain embodiments, these antimicrobial, copolypeptide compositions may have a block-sequence structure, including one or more blocks containing segments of 2 or more consecutive cationic amino acids/monomer (e.g., lysine, arginine), or segments of 2 or more consecutive hydrophobic amino acids/monomer (e.g., leucine, isoleucine, valine, alanine, phenylalanine). In certain cases, triblock or multiblock compounds (i.e., several blocks of distinct amino acids, monomers and/or other polymer blocks) may be particularly effective. Blocks of alternating amino acids or monomers may also be effective, while blocks of random sequences may also be advantageous in certain settings. Other embodiments may also feature a copolypeptide block or segment of the same amino acid/monomer or different amino acids/monomers that are chemically attached to a different polymer. It is also anticipated that the bioactivity and chemical composition of block copolypeptides/copolymers may be more reproducible from batch to batch than that of random copolypeptides/copolymers. It is also anticipated that block copolypeptides may be less immunogenic than random copolypeptides. Blocks may be composed of natural and/or unnatural amino acids that display different degrees of hydrophilicity or hydrophobicity. Natural amino acids (hydrophobic, such as but not limited to alanine, glycine, isoleucine, leucine, phenylalanine, valine, and hydrophilic, such as but not limited to arginine, esparto acid, asparagine, glutamic acid, glutamine, tysine, serine, tyrosine, or threonine) or unnatural amino acids, such as but not limited to fluorinated or unsaturated hydrocarbons can be used, as well as enantiopure or racemic mixtures. In addition to polypeptidic materials or hybrids containing synthetic polymers and peptidic segments or blocks, may also display increased antimicrobial activity, decreased mammalian toxicity, or both. For example, a hydrophobic polypeptide may be conjugated to a hydrophilic polymer or oligomer, or a hydrophobic synthetic polymer or oligomer may be conjugated to a hydrophilic peptide and display similar characteristics than a material composed entirely of linked amino acids. A peptidic segment, block or domain can also be replaced by a synthetic oligomeric or polymeric segment, including direct incorporation into the polymer backbone, or as a graft.

We have demonstrated that block-sequence structure can be used to direct molecular self-association or self-assembly. For example, we demonstrated by determining the critical aggregation concentration (CAC) that block-sequence copolypeptide $K_{55}L_{20}$ exhibits a substantially stronger self-association (CAC=0.33 uM) than random-sequence $K_{55}L_{20}$ (CAC=160 uM). This molecular design element is important in preferred embodiments of our invention that involve designed hierarchical structures.

Designed Hierarchical Structures.

These compositions may be formulated as hierarchical structures, such as multimers, micelles, hydrogels, or vesicles, or mixtures thereof. Enhanced antimicrobial activity, or decreased mammalian toxicity, or both may be derived from the organization of the antimicrobial elements into high order structures that either display the actives in a more efficient way or with a higher local concentration. For example, the higher density of cationic charge at the hydrophilic sections of the liquid interface of an emulsion may lead to better interaction with microbial organisms. In a similar way, other high order structures such as vesicles, micelles, lamella, or hydrogels may be able to deliver the antimicrobial elements more effectively than an isolated antimicrobial element alone. On the other hand, the secondary interactions present, and sometimes responsible for the higher ordered structures of the hydrophobic segments in amphiphilic polymers, may be responsible for the reduced mammalian toxicity.

These designed synthetic copolypeptides may self-assemble into hierarchical structures (e.g., multimers, micelles, emulsions, hydrogels, vesicles) thereby enhancing antimicrobial activity (in vitro or in vivo), decreasing toxicity, or both. Moreover, these compounds may easily precipitate onto and/or directly bind to damaged tissues where they may provide a local, concentrated antimicrobial activity.

In certain embodiments, these compositions may be formulated as, or mixed into, emulsions, micro-emulsions or nanoemulsions. In particular, these emulsions may be designed to have high antimicrobial activity, low mammalian toxicity, or both. It is recognized that these activities may depend on one or more additional factors, such as the composition of the oil phase, or droplet size.

In certain embodiments, these antimicrobial copolypeptides may be formulated as hydrogels. These antimicrobial molecules would self-assemble into hydrogels. It is anticipated that there would be advantages to physical hydrogels, which are inherently antimicrobial that may be able to pass through small bore openings (e.g., 20 gauge needles) or into small tissue spaces and then rapidly re-gel. These hydrogel forming antimicrobial copolypeptides may be designed to be mildly tissue adherent and optically clear. It is anticipated that they will provide localized, concentrated antimicrobial activity, as well as the benefits of standard hydrogels (e.g., fluid retention). The antimicrobial properties of the copolypeptides that self-assemble into fibrils that form hydrogels have been demonstrated at concentrations well below the gelation concentration. For example $K_{180}L_{20}$ has been shown to be a potent antimicrobial at concentrations of 10 ug/ml, while its gelation concentration is approx. 10 mg/ml. This establishes that the material is inherently antimicrobial, while at the same time can self-associate to hierarchical structures that provide macroscopic properties to the preparations. Also, $K_{180}L_{20}$ at hydrogel forming concentrations (e.g., 20 mg/ml) has been shown to be an effective antimicrobial in infection prevention model in vivo, as well as to have low toxicity in several models in vivo.

Long Chain Length.

In certain embodiments, these antimicrobial copolypeptide compositions may have a relatively long chain length (e.g., over 100 amino acids). It is anticipated that synthetic copolypeptides with longer chain length can be optimized to display increased efficacy, decreased mammalian toxicity or both in certain settings. Notably, they may display multiple active sites, conformations, domains, or fragments more effectively and therefore could continue to display antimicrobial activity even after partial complexation or degradation. Long-chain copolypeptides may interact more effectively with microbial surfaces, and interact with more than one microbe at a time. Longer polypeptides may be able to disrupt bacterial membranes more effectively by cross-linking of the negative components of the bacterial membrane. They may also be able to interact with certain soluble biomolecules or tissue components, while leaving a molecular segment free to interact with microbes.

Low Hydrophobe Content.

These compositions may have low molar fractions of hydrophobic monomer (e.g., leucine, isoleucine, valine, alanine, phenylalanine, or non-peptidic hydrophobic monomer) by comparison to other antimicrobial peptides, for example 35% or less. In the present invention, we recognize that block copolypeptides with a low molar fraction of hydrophobic monomers (e.g., $f_{HM}$=8%, 18%, 25%, 35%) can yield high antimicrobial activity and low mammalian toxicity. Such compounds may overcome specific limitations inherent to copolymers with high $f_{HM}$. Amphiphilic copolymers with low $f_{HM}$ offer several distinct advantages. For example, it is anticipated that reduced hydrophobic content decreases mammalian toxicity. It has been reported that increased hydrophobic content in antimicrobial peptides increases hemolytic activity, possibly by reducing selectivity for bacterial over mammalian cell membranes [22]. Other advantages may include improved solubility in aqueous solution. Some compositions of the present invention incorporate low $f_{HM}$. Specifically, we have demonstrated high antimicrobial activity with mole fraction of hydrophobic monomers as low as about 8%. Furthermore, we have shown that high antimicrobial activity can be attained by either decreasing the hydrophobic content or by increasing the hydrophilic content.

Enantiopurity Influences Secondary Structure.

In certain embodiments, the enantiopurity of the amino acids (especially in the hydrophobic domain) can be used to control self-assembly characteristics. By example, we demonstrated that $K_{55}L_{20}$ and $K_{55}(rac-L)_{20}$ both achieve reduction of bacteria, for both a Gram-positive (*S. aureus*) and Gram-negative (*E. coli, P. aeruginosa*) strains at a very low concentration (10 μg/ml). Racemic mixtures, or mixtures with varying optical purity, may offer improved solubility and reduced aggregation. Importantly, incorporation of a fraction of D-amino acids may have particular advantages in therapeutic applications against biofilms [38]. Moreover, decreasing optical purity removes ordered secondary structure, which influences self-association and/or self assembly characteristics. For example, we demonstrated by determining the critical aggregation concentration (CAC) that block-sequence copolypeptide $K_{55}L_{20}$ exhibits a stronger association (CAC=0.33 uM) than $K_{55}(rac-L)_{20}$ (CAC=8.1 uM).

Solution Metastability.

In certain embodiments, these antimicrobial, copolypeptide compositions can be designed with relatively low solution stability. Moreover, these materials can be designed to bind to/precipitate at sites where they interact with negatively charged elements found commonly on microbes (e.g., bacterial micro-colonies and biofilms) and at sites of tissue damage. These solution "metastable" antimicrobial molecules may easily precipitate (for example, when interacting with microbes or mammalian tissue materials of opposite charge). Certain advantages may be derived from synthetic copolypeptides that easily precipitate onto and/or directly bind to damaged tissues where they may provide a local, concentrated antimicrobial activity. Moreover, antimicrobial copolypeptides (or other antimicrobial materials) may be made more effective in certain settings by binding to/precipitating at sites of microbes (e.g., bacterial micro-colonies and biofilms). Certain design elements may be incorporated so that synthetic copolypeptide hierarchical structures remain completely solvated in the absence of biological materials (e.g., serum, wound fluids, damaged tissues, bacterial biofilms), but become metastable upon binding biological materials. Once the antimicrobial materials become metastable, they may settle on tissues or bacterial colonies, thus dramatically increasing the local concentration acting as an antimicrobial agent and/or as an antimicrobial barrier.

Multivalency.

In certain embodiments, these compositions may be engineered to include multiple antimicrobial sites. These antimicrobial sites may include local regions of cationic charge and/or local regions of hydrophobicity. Therefore, a single material could have several different active sites capable of killing/inhibiting microbes. In this way, a single supramolecular construct could effect a "multi-hit" approach, providing greater effectiveness and further decreasing the likelihood of microbial resistance. In addition, additive or synergistic activity may be observed. In addition, the material may release antimicrobial fragments as it is degraded.

Microbe Selectivity.

These compositions can be engineered to preferentially target certain microbes over others. Notably, targeting traditionally pathogenic organisms (e.g., *S. aureus*, methicillin-resistant *S. aureus* (MRSA)) over traditionally normal flora (e.g., *P. acnes*), may be of particular benefit. Furthermore, targeting of selected viruses, bacteria or fungi may be relevant to particular clinical settings, such as use in a hand sanitizer or in prevention of wound infections. We have developed multiple synthetic copolypeptides that have shown higher activity against *S. aureus* than against *P. acnes* in vitro.

Mixtures.

In certain embodiments, these compositions may be formulated with two or more distinct antimicrobial copolypeptides/copolymers. In this way, a composition could affect a "two-hit" approach, providing greater effectiveness and further decreasing the development of microbial resistance. In addition, additive or synergistic activity may be observed.

In certain embodiments, these compositions may be synthesized with chemical modification of monomer amino acids or residues, for example, conversion of a primary amine (e.g., of lysine monomer) to a guanidinium group. Other modifications may include alkylation, acylation, amidation, halogenation, transesterification, reductive amination or other chemical transformations which add functionality or modifies existing functionality of the monomer amino acids or residues.

In certain embodiments, these compositions may be formulated with different classes of other antimicrobial agents (e.g. alcohol, chlorine-based compounds, quaternary ammonium compounds, phenolic compounds, chlorhexidine, antibiotics, antibodies). This may include mixing in the compositions of the invention with known antimicrobial agents. It may include formulating synthetic copolypeptides/copolymers as a type of delivery agent or depot (e.g., emulsion, double nanoemulsion, vesicle, hydrogel) and incorporating one or more additional antimicrobial substances.

In certain embodiments, these compositions may be formulated with bioactive materials or other active pharmaceutical ingredients (APIs). In this way, the formulations could provide antimicrobial activity, as well as a second or third function. Possibilities include, but are not limited to hemostatic materials, growth factors to support wound healing, pro- or anti-inflammatory agents, and immune modulators.

In certain embodiments, the synthetic antimicrobial copolypeptides/copolymers may be designed to contain other bioactive elements (e.g., specific sequences, blocks, hierarchical structures or chemical modifications). For example, they may contain elements that would promote hemostasis by one or more mechanisms such as platelet binding, platelet activation, acceleration of coagulation, decrease of fibrinolysis, absorption of fluid or physical barrier effects. This invention envisions synthetic copolypeptides that are hemostatic in nature, as well as those that have combined antimicrobial and hemostatic activities (FIGS. 27-32, FIG. 39 (Table 7)).

Experimental

General.

Dry tetrahydrofuran (THF) was prepared by passing it through a column packed with alumina under nitrogen prior to use. Molecular weights (Mn) and polydispersities (PDIs) were obtained by tandem gel permeation chromatography/ light scattering (GPC/LS) performed at 60° C. on a SSI pump equipped with a Wyatt DAWN EOS light scattering detector and Wyatt Optilab DSP with $10^5$, $10^4$, and $10^3$ Å Phenomenex 5 μm columns using 0.1 M LiBr in DMF as eluent and polypeptide concentration of approximately 5 mg/mL. Fourier transform infrared spectra (FTIR) were recorded on a Perkin Elmer RX1 FTIR Spectrophotometer calibrated using polystyrene film. $^1$H NMR spectra were recorded on a Bruker AVANCE 400 MHz spectrometer. Deionized (DI) water was purified using a Purelab Option 560 reverse osmosis purifier. Millipore water was obtained from a Millipore Milli-Q Biocel A10 purification unit.

Block Copolypeptide Synthesis—General.

The α-amino acid-N-carboxyanhydride NCA monomers were synthesized using previously published literature protocols. All of the block copolypeptides were polymerized using the $(PMe_3)_4Co$ initiator. The resulting polypeptides were characterized using GPC, $^1$H NMR and IR spectroscopy. The compositions of the copolymers were determined by analysis of the integration values of the $^1$H NMR spectra recorded in d-TFA. All compositions were found to be within 5% of predicted values. Polymer chain length distributions ranged (Mw/Mn) from 1.1 to 1.3.

Poly($N_\epsilon$-CBZ-L-lysine)$_{55}$-b-poly(rac-leucine)$_{20}$. Z-K$_{55}$(rac-L)$_{20}$.

In the drybox, $N_\epsilon$-CBZ-L-tysine, Z-K NCA (11.34 g, 37 mmol) was placed in a 500 mL flat bottom flask with a stir bar. Dry THF (227 mL) was added and then sealed with a plastic stopper. An aliquot of $(PMe_3)_4Co$ (18.9 mL of a 40 mg/mL in dry THF, 2.1 mmol) was then added via syringe and the flask sealed and stirred for 45 minutes. An aliquot (50 μL) was removed from the polymerization for GPC analysis (Mn=14.7×10$^3$ g/mol, Mw/Mn=1.12). The stock poly($N_\epsilon$-CBZ-L-lysine)$_{55}$ was then divided equally among 8 fractions (0.26 mmol $(PMe_3)_4Co$ initiator in each) and placed in 125 mL flat bottomed flasks. To each fraction, a different amount of hydrophobic D,L NCA was added as needed. For example, to synthesize Z-K$_{55}$(rac-L)$_{20}$ an aliquot of D,L leucine (L) NCA (5.3 mL of a 50 mg/mL in THF, 1.7 mmol) was added and allowed to polymerize overnight.

A similar procedure was used to produce the following block copolymers: Z-K$_{55}$(rac-L)$_5$, D,L leucine NCA (1.3 mL of a 50 mg/mL in THF, 0.42 mmol); Z-K$_{55}$(rac-L)$_{10}$, D,L leucine NCA (2.7 mL of a 50 mg/mL in THF, 0.84 mmol); Z-K$_{55}$(rac-L)$_{30}$, D,L leucine NCA (7.9 mL of a 50 mg/mL in THF, 2.5 mmol); Z-K$_{55}$(rac-I)$_{20}$, D,L isoleucine (I) NCA (5.3 mL of a 50 mg/mL in THF, 1.7 mmol); Z-K$_{55}$(rac-L/F)$_{20}$, D,L leucine NCA (2.6 mL of a 50 mg/mL in THF, 0.84 mmol) and D,L phenylalanine (F) NCA (3.2 mL of a 50 mg/mL in THF, 0.84 mmol); Z-K$_{55}$(rac-A)$_{20}$, D,L alanine (A) NCA (3.9 mL of a 50 mg/mL in THF, 1.7 mmol); and Z-K$_{55}$(rac-V)$_{20}$, D,L valine (V) NCA (5.3 mL of a 50 mg/mL in THF, 1.7 mmol).

Poly(L-Lysine.HCl)$_{55}$-b-poly(rac-Leucine)$_{20}$, K$_{55}$(rac-L)$_{20}$.

The poly($N_\epsilon$-CBZ-L-lysine)$_{55}$-b-poly(rac-leucine)$_{20}$ was removed from the drybox. The THF was removed under reduced pressure then dissolved in trifluoroacetic acid (TFA) (50 mL). Next, the flask was placed in an ice bath followed by the addition of HBr (33% in acetic acid, 6.0 mL, 19.7 mmol) and stirred for two hrs. The deprotected polymer was isolated by addition of diethyl ether to the reaction mixture (50 mL), followed by centrifugation (three min at 3,000 rpm). The precipitated polymer was then washed and centrifuged two more times with diethyl ether. The isolated polymer was then dissolved in Millipore water and dialyzed (2,000 MWCO membrane) against tetrasodium EDTA (3 mmol, four days), 0.1 M HCl (two days), DI water (one day), 0.1 M NaCl (two days), Millipore water (two days), changing each solution two times/day. The dialyzed polymer was isolated by freeze-drying to give the product as a dry white powder (0.80 g, 84%).

A similar procedure was used to produce the following block copolymers: K$_{55}$(rac-L)$_5$ (0.51 g, 62%), K$_{55}$(rac-L)$_{10}$ (0.70 g, 81%), K$_{55}$(rac-L)$_{30}$ (0.77 g, 74%), K$_{55}$(rac-L)$_{20}$ (0.78 g, 81%), K$_{55}$(rac-L/F)$_{20}$ (0.74 g, 79%), K$_{55}$(rac-A)$_{20}$ (0.82 g, 92%), and K$_{55}$(rac-V)$_{20}$ (0.82 g, 88%).

Poly(ethylene glycol)$_{205}$-b-poly(rac-leucine)$_{20}$, PEG$_{204}$(rac-L)$_{20}$.

Prior to use, 0.50 g of ω-amino terminated poly(ethylene glycol) monomethyl ether, PEG$_{205}$-NH$_2$, (Mn=9,000 g/mol, PDI=1.08) was dried by dissolving in dry benzene followed by removal of the solvent by distillation to yield a dry solid. In a drybox, PEG$_{205}$-NH$_2$ (0.50 g, 5.6×10$^4$ moles) was dissolved in 4.0 mL of dry DMF. Next, L-Leucine NCA (83 mg, 0.53 mmol) and D-Leucine NCA (83 mg, 0.53 mmol) were dissolved in dry DMF (2.5 mL) and then added to the polymerization mixture. The solution stirred for three days at room temperature until fully polymerized. It was then removed from the drybox and 5 mL of Millipore water was added and then transferred to a dialysis membrane (2,000 MWCO membrane) and dialyzed against Millipore water (three days), changing each solution two times/day. The dialyzed polymer was isolated by freeze-drying to give the product as a dry white powder (0.51 g, 82%). $^1$H-NMR Poly(L-glutamate-Na)$_{54}$-b-poly(rac-leucine)$_{20}$, E$_{64}$(rac-L)$_{20}$.

In the drybox, γ-benzyl-L-glutamate, Bzl-Glu NCA (5.00 g, 19 mmol) was placed in a 250 mL flat bottom flask with a stir bar. Dry THF (100 mL) was added and then sealed with a plastic stopper. An aliquot of (PMe$_3$)$_4$Co (11.5 mL of a 40 mg/mL in dry THF, 1.27 mmol) was then added via syringe and the flask sealed and stirred for 1 hour. An aliquot (50 µL) was removed from the polymerization for GPC analysis (Mn=13.9×10$^3$ g/mol, Mw/Mn=1.27). Next, an aliquot of D,L leucine (L) NCA (18.7 mL of a 50 mg/mL in THF, 6.0 mmol) was added and allowed to polymerize overnight. Next, the THF was removed under reduced pressure and then dissolved in dry CH$_2$Cl$_2$ (100 ml). To remove the benzyl protecting groups, iodotrimethylsilane was added via syringe (10.8 mL, 76 mmol). A reflux condenser was attached to the flask and refluxed overnight at 40° C. Next, the solvent was removed under reduced pressure and 1 M NaOH was added and stirred overnight, then filtered to remove precipitate and dialyzed (6-8,000 MWCO membrane) against 5 mM sodium bisulfite and 0.1 M NaOH (three days), then Millipore water (four days), changing each solution two times/day. The clear solution was then freeze dried to afford a white fluffy solid (1.26 g, 36%).

Poly(L-homoarginine-HCl)$_{55}$-b-poly(rac-Leucine)$_{20}$, R$^H_{55}$(rac-L)$_{20}$.

To a 500 mL round bottom flask containing a stir bar, K$_{55}$(rac-L)$_{20}$ (1.00 g, 0.09 mmol) was added and then dispersed in 1 M NaOH (137 mL). Next, 3,5-dimethyl-1-pyrazole formamidinium nitrate was added (3.93 g, 19.6 mmol). The pH was adjusted to pH=10 using HCl and then placed into a 40° C. oil bath and stirred for 48 hours. To quench the reaction, the solution was acidified with 0.1 M HCl to a pH=3 then placed in a dialysis bag (2,000 MWCO) and dialyzed against Millipore water (five days), changing each solution two times/day. The dialyzed polymer was isolated by freeze-drying to give the product as a white powder (0.95 g, 78%).

Poly(L-Lysine HCl)$_{60}$-co-poly(L-Lysine)$_{60}$, K$_{60}$(rac-L)$_{20}$. To a 50 mL polypropylene centrifuge tube containing a stir bar, Poly(L-Lysine.HCl)$_{80}$, K$_{80}$(75 mg, 5.7 µmol) was added and then dissolved in 50 mM 2-(N-morpholino)ethanesulfonic acid (MES) buffer (15 mL). Next, tetrahydrofuran (THF) was added (14.3 mL). To this solution, N-hydroxy succinimide (530 µL of a 10 mg/mL solution in THF/water, 46 µmol), octanoic acid (660 µL of a 10 mg/mL solution in THF, 46 µmol), and 1-Ethyl-3-(3-dimethylaminopropyl)carbodiimide (2.6 mL of a 50 mg/mL solution in THF/water, 0.68 mmol) were added. The solution was allowed to stir overnight. The next day, the solution was placed into a dialysis bag (2,000 MWCO) and dialyzed against Millipore water (three days), 0.01 M HCl (two days), 0.01 M NaOH (one day), 0.01 M HCl (one day), Millipore water (two days), changing each solution two times/day. The dialyzed polymer was isolated by freeze-drying to give the product as a white powder (68 mg, 85%).

Critical Aggregation Concentration (CAC) Via Pyrene Fluorescence.

Polypeptide solutions (2 mL) were dispersed in water at a range of concentrations (2.0×10$^{-3}$ to 2.0×10$^{-12}$ M). A stock pyrene solution was made by dissolving pyrene in acetone (6.0×10$^{-2}$ M). Next, an appropriate amount of the pyrene stock solution was added to give a final concentration of 12×10$^{-7}$ M in water and the acetone was evaporated off. To each polypeptide solution, 2.0 mL of the aqueous stock pyrene solution was added to afford a final concentration of 6.0×10$^{-7}$ M. Then, each solution was allowed to equilibrate overnight prior to measurements. To record fluorescence spectra, 3.0 mL of each polypeptide solution was added to a 4.0 mL polystyrene covet. The excitation spectra were recorded within a range of 300-360 nm at an emission wavelength of 390 nm. All spectra were run with an integration time of 1 sec/0.5 nm. The ratio of the intensities of two peaks I338/I333 was plotted as a function of polypeptide concentration (M) for each sample. The CACs were determined as the intersection of the extrapolated linear fits of the plot.

Emulsion Preparation.

In a typical formulation, 800 µL of a 1 w/v % polypeptide solution was added to a 1.5 mL sterile centrifuge tube. Next, 200 µL of oil phase, typically polydimethylsiloxane (PDMS) with a viscosity of 10 cSt (sterilized by filtered through a 0.2 µm sterile filter), was added to give a final volume fraction, φ=0.2. The solution was emulsified for one minute using a hand-held ultrasonic homogenizer (Cole-Parmer 4710 Series Model ASI at an output of 35-40%) to form nanoscale droplets (~400-500 nm in diameter based on dynamic light scattering DLS measurements).

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

REFERENCES

1. Gilbert, P.a.M., L. E., *Cationic antiseptics: diversity of action under a common epithet*. Journal of Applied Microbiology, 2005. 99(4): p. 703-715.
2. Lio, P., A. and Kaye, E., T., *Topical antibacterial agents*. Infectious Disease Clinics of North America, 2009. 23(4): p. 945-963.
3. Landman, D., et al., *Polymyxins revisited*. Clin Microbiol Rev, 2008. 21(3): p. 449-65.
4. Stickler, D. J. and B. Thomas, *Antiseptic and antibiotic resistance in Gram-negative bacteria causing urinary tract infection*. J Clin Pathol, 1980. 33(3): p. 288-96.
5. Higgins, C. S., et al., *Resistance to antibiotics and biocides among non-fermenting Gram-negative bacteria*. Clinical Microbiological Infections, 2001. 7: p. 308-315.
6. Boyce, J. M.a.P., D., *Guideline for Hand Hygiene in Health-Care Settings*. Morbidity and Mortality Weekly Report, 2002. 51(RR-16): p. 1-54.

7. Eberlein, T.a.A., O., *Clinical use of polihexanide on acute and chronic wounds for antisepsis and decontamination.* Skin Pharmacology and Physiology. 2010. 23 Suppl: p. 45-51.

8. Oie, S. and A. Kamiya, *Microbial contamination of antiseptics and disinfectants.* Am J Infect Control, 1996. 24(5): p. 389-95.

9. Zasloff, M., *Antimicrobial peptides of multicellular organisms.* Nature, 2002. 415(6870): p. 389-95.

10. Zaiou, M., *Multifunctional antimicrobial peptides: therapeutic targets in several human diseases.* J Mol Med (Berl), 2007. 85(4): p. 317-29.

11. Hancock, R. E. and R. Lehrer, *Cationic peptides: a new source of antibiotics.* Trends Biotechnol, 1998. 16(2): p. 82-8.

12. Yeaman, M. R. and N. Y. Yount, *Mechanisms of antimicrobial peptide action and resistance.* Pharmacol Rev. 2003. 55(1): p. 27-55.

13. Brogden, K. A., *Antimicrobial peptides: pore formers or metabolic inhibitors in bacteria?* Nat Rev Microbiol, 2005. 3(3): p. 238-50.

14. Bani-Jaber, A., et al., *Efficacy of the Antimicrobial Peptide Nisin in Emulsifying Oil in Water.* Journal of Food Science. 2000. 65(3): p. 502-506.

15. Salick, D. A., et al., *Inherent antibacterial activity of a peptide-based beta-hairpin hydrogel.* J Am Chem Soc, 2007. 129(47): p. 14793-9.

16. Liu, D. and W. F. DeGrado, *De novo design, synthesis, and characterization of antimicrobial beta-peptides.* J Am Chem Soc, 2001. 123(31): p. 7553-9.

17. Epand, R. F., at al., *Dual mechanism of bacterial lethality for a cationic sequence-random copolymer that mimics host-defense antimicrobial peptides.* J Mol Biol, 2008. 379 (1): p. 38-50.

18. Porter, E. A., B. Weisblum, and S. H. Gellman, *Mimicry of host-defense peptides by unnatural oligomers: antimicrobial beta-peptides.* J Am Chem Soc, 2002. 124(25): p. 7324-30.

19. Gabriel, G. J., et al., *Infectious Disease: Connecting Innate Immunity to Biocidal Polymers.* Mater Sci Eng R Rep, 2007. 57(1-6): p. 28-64.

20. Liu, D., et al., *Nontoxic membrane-active antimicrobial alylamide oligomers.* Angew Chem Int Ed Engl, 2004.43 (9): p. 1158-62.

21. Tew, G. N., et al., *Antimicrobial activity of an abiotic host defense peptide mimic.* Biochim Biophys Acta, 2006. 1758 (9): p. 1387-92.

22. Ilker, M. F., et al., *Tuning the hemolytic and antibacterial activities of amphiphilic polynorbornene derivatives.* J Am Chem Soc, 2004. 126(48): p. 15870-5.

23. Kuroda, K., G. A. Caputo, and W. F. DeGrado, *The role of hydrophobicity in the antimicrobial and hemolytic activities of polymethacrylate derivatives.* Chemistry, 2009. 15(5): p. 1123-33.

24. Wang, Y., at al., *Antimicrobial and Hemolytic Activities of Copolymers with Cationic and Hydrophobic Groups: A Comparison of Block and Random Copolymers.* Macromolecular Bioscience, 2011: p. n/a-n/a.

25. Goodson, B., et al., *Characterization of novel antimicrobial peptoids.* Antimicrob Agents Chemother, 1999. 43(6): p. 1429-34.

26. Deming, T. J., *Polypeptide and Polypeptide Hybrid Copolymer Synthesis via NCA Polymerization.* ChemInform, 2007. 38(5): p. no-no.

27. Deming, T. J., *Methodologies for preparation of synthetic block copolypeptides: materials with future promise in drug delivery.* Advanced Drug Delivery Reviews, 2002. 54: p. 1145-1155.

28. Wyrsta, M. D., *Synthesis and studies of polypeptide materials: Self-assembled block copolypeptide amphiphiles, DNA-condensing block copolypeptides and membrane-interactive random copolypeptides,* 2002, University of California, Santa Barbara. p. 125.

29. Wyrsta, M. D., A. L. Cogen, and T. J. Deming, *A parallel synthetic approach for the analysis of membrane interactive copolypeptides.* J Am Chem Soc. 2001. 123(51): p. 12919-20.

30. Deming, T. J., *Synthetic polypeptides for biomedical applications.* Progress in Polymer Science, 2007. 32: p. 858-875.

31. Zhou, C., et al., *High potency and broad-spectrum antimicrobial peptides synthesized via ring-opening polymerization of alpha-aminoacid-N-carboxyanhydrides.* Biomacromolecules, 2010. 11(1): p. 60-7.

32. Yang, C. Y., et al., *Biocompatibility of amphiphilic diblock copolypeptide hydrogels in the central nervous system.* Biomaterials, 2009. 30: p. 2881-2898.

33. Hanson, J. A., et al., *Nanoscale double emulsions stabilized by single-component block copolypeptides.* Nature, 2008. 455: p. 85-89.

34. Ho, Y.-T., S. Ishizaki, and M. Tanaka, *Improving emulsifying activity of [var epsilon]-polylysine by conjugation with dextran through the Maillard reaction.* Food Chemistry, 2000. 68(4): p. 449-455.

35. Lam, H., et al., *D-amino acids govern stationary phase cell wall remodeling in bacteria.* Science, 2009. 325(5947): p. 1552-5.

What is claimed is:

1. An antimicrobial composition comprising:
    at least one species of synthetic copolypeptide of at least forty amino acid residues comprising:
        at least one hydrophilic segment containing at least five contiguous cationic amino acid residues; and
        at least one hydrophobic segment containing at least five contiguous hydrophobic amino acid residues;
        wherein the hydrophilic segment contains a larger number of amino acid residues than the hydrophobic segment; and
    water;
    wherein said at least one species of synthetic copolypeptide forms multimeric structures in aqueous media;
    wherein said at least one species of synthetic copolypeptide inhibits or kills microbes in aqueous media; and
    wherein the composition inhibits or kills microbes.

2. The composition as described in claim 1, wherein said at least one species of synthetic copolypeptide comprises substantially only natural amino acids.

3. The composition as described in claim 1, wherein the ratio of the number of amino acids in said hydrophilic segment to the number of amino acids in said hydrophobic segment is at least 1.8 to 1.

4. The composition as described in claim 1, wherein the structures formed in aqueous media are selected from the group consisting of multimers in solution, micelles, sheets, vesicles, and fibrils.

5. The composition as described in claim 1, wherein said at least one species of synthetic copolypeptide is characterized by the ability to form mixtures in water without visible precipitate at room temperature at concentrations up to 10 fold above the critical aggregation concentration (CAC).

6. The composition as described in claim 1, wherein said at least one species of synthetic copolypeptide is characterized by the ability to form mixtures in water without visible precipitate at room temperature at concentrations up to 100 fold above the critical aggregation concentration (CAC).

7. The composition as described in claim 1, wherein said at least one species of synthetic copolypeptide has a critical aggregation concentration (CAC) in water that is at least 1 log lower than that of a random sequence copolypeptide of the same amino acid composition.

8. The composition as described in claim 1 characterized in that it kills or inhibits microbes in vitro at a lower concentration than it kills mammalian cells in vitro.

9. The composition as described in claim 1 characterized in that it kills or inhibits microbes in or on mammalian tissues in vivo at concentrations that show low toxicity for those tissues.

10. The composition as described in claim 1 characterized in that said at least one species of synthetic copolypeptide forms mixtures in water without visible precipitate at room temperature at concentrations of at least 1000 µg/mL.

11. The composition as described in claim 1 characterized in that it kills or inhibits microbes in vitro as measured by greater than 3 logs killing of *Staphylococcus epidermidis* and *Escherichia coli* in standard 60 minute time-kill assays at concentrations of said at least one species of synthetic copolypeptide of 100 µg/mL or less.

12. The composition as described in claim 1 characterized in that said at least one species of synthetic copolypeptide forms mixtures in water without visible precipitate at room temperature at concentrations at least 10 fold above the concentration required to inhibit or kill microbes in vitro as measured by greater than 3 logs killing of *Staphylococcus epidermidis* and *Escherichia coli* in standard 60 minute time-kill assays.

13. The composition as described in claim 1 having a storage modulus of at least 50 Pa at a concentration of said at least one species of synthetic copolypeptide of less than 40 mg/mL.

14. The composition as described in claim 1, wherein said at least one species of synthetic copolypeptide promotes platelet aggregation.

15. The composition as described in claim 1, wherein said at least one species of synthetic copolypeptide inhibits fibrinolysis.

16. The composition as described in claim 1 further comprising a combination of immiscible phases in a dispersed mixture or emulsion.

17. The composition as described in claim 1 formulated as a solution, a gel, a cream, a foam, or a dressing.

18. The composition as described in claim 1, further comprising an added active pharmaceutical ingredient (API) selected from steroids, pro-inflammatory agents, anti-inflammatory agents, anti-acne agents, preservatives, hemostatic agents, angiogenic agents, wound healing agents, anti-cancer agents and other antimicrobial agents.

19. The use of the composition as described in claim 1 for prevention or treatment of infection, for topical anti-infection, for microbial decolonization, for wound treatment, for surgical site treatment, for trauma treatment, for burn treatment, for treatment of diabetic foot ulcers, for eye treatment, for vaginal infections, for urinary tract infections, for hand sanitization, for coating prosthetic devices and implants, for food preservation and for solution preservation.

20. A method for the prevention or treatment of infections in a mammal comprising the step of:
  applying to a site an antimicrobial composition comprising:
    at least one species of synthetic copolypeptide of at least forty amino acid residues comprising:
      at least one hydrophilic segment containing at least five contiguous cationic amino acid residues; and
      at least one hydrophobic segment containing at least five contiguous hydrophobic amino acid residues;
      wherein the hydrophilic segment contains a larger number of amino acid residues than the hydrophobic segment; and
    water;
  wherein said at least one species of synthetic copolypeptide forms multimeric structures in aqueous media;
  wherein said at least one species of synthetic copolypeptide inhibits or kills microbes in aqueous media; and
  wherein the composition inhibits or kills microbes.

* * * * *